US007006894B2

(12) United States Patent
de la Huerga

(10) Patent No.: US 7,006,894 B2
(45) Date of Patent: Feb. 28, 2006

(54) INTERACTIVE MEDICATION CASSETTE

(76) Inventor: Carlos de la Huerga, 9190 N. Upper River Rd., River Hills, WI (US) 53217

( * ) Notice: Subject to any disclaimer, the term of this patent is extended or adjusted under 35 U.S.C. 154(b) by 28 days.

(21) Appl. No.: 10/649,805

(22) Filed: Aug. 26, 2003

(65) Prior Publication Data

US 2004/0039481 A1   Feb. 26, 2004

Related U.S. Application Data

(60) Division of application No. 09/168,783, filed on Oct. 8, 1998, now Pat. No. 6,611,733, and a continuation-in-part of application No. 08/955,475, filed on Oct. 21, 1997, now Pat. No. 6,032,155, and a continuation-in-part of application No. 08/832,613, filed on Mar. 28, 1997, now Pat. No. 5,852,590.

(60) Provisional application No. 60/096,269, filed on Aug. 12, 1998, provisional application No. 60/033,491, filed on Dec. 20, 1996.

(51) Int. Cl.
*G07F 17/00* (2006.01)

(52) U.S. Cl. .................. 700/244; 700/236; 700/234; 700/235

(58) Field of Classification Search ............... 700/236, 700/244, 234, 235; 368/10, 11
See application file for complete search history.

(56) References Cited

U.S. PATENT DOCUMENTS

| 4,368,988 A | 1/1983 | Tahara et al. ............ 368/63 |
| 4,384,288 A | 5/1983 | Walton ................... 340/5.8 |
| 4,476,381 A | 10/1984 | Rubin .................... 235/375 |

(Continued)

FOREIGN PATENT DOCUMENTS

GB    1400317    7/1975

(Continued)

*Primary Examiner*—Donald P. Walsh
*Assistant Examiner*—Michael E. Butler
(74) *Attorney, Agent, or Firm*—Andrus, Sceales, Starke & Sawall, LLP

(57) ABSTRACT

This invention relates to an interactive medication cassette with a machine readable and writable information strip that contains information corresponding to the medication in the cassette. The interactive medication cassette holds the medication and couples the corresponding information to the medication. The cassette is designed for use in a medication distribution and inventory system that includes at least one medication dispensing machine having a sensor for reading the information in the strip and updating or altering this information when medication is added to or removed from the cassette. The cassette travels with the medication during the distribution of the medication to a patient, and its information is reported to one or more memory devices or hospital or pharmacy data base during this process. The cassette is filled by a pharmacy dispensing machine holding a bulk container filled with a particular type of medication and a singulator for counting the quantity of medication added to the cassette. The pharmacy dispensing machine alters the information strip to include medication and quantity information corresponding to the dispensed medication. The cassette is closed and locked to prevent unauthorized access during transport to a hospital floor workstation. A hospital floor dispensing machine incrementally dispense the medication from the cassette, and updates the information strip with additional information including the quantity of medication dispensed from the cassette. When the cassette is returned to the pharmacy and its unused contents is emptied into the bulk container, the information strip on the cassette automatically updates an information strip on the bulk container to indicate the number of doses of medication added to the bulk container. In this manner, a reliable medication distribution and inventory system is achieved while maintaining improved control over the access to the medication on the hospital floor.

7 Claims, 19 Drawing Sheets

U.S. PATENT DOCUMENTS

| | | | | |
|---|---|---|---|---|
| 4,575,621 A | 3/1986 | Dreifus | | 235/380 |
| 4,598,275 A | 7/1986 | Ross et al. | | 340/573.4 |
| 4,674,652 A | 6/1987 | Aten | | 221/3 |
| 4,694,284 A | 9/1987 | Leveille et al. | | 340/574 |
| 4,717,261 A | 1/1988 | Kita et al. | | 368/63 |
| 4,730,849 A | 3/1988 | Siegel | | 283/70 |
| 4,733,797 A | 3/1988 | Haber | | 221/8 |
| 4,811,764 A * | 3/1989 | McLaughlin | | 141/98 |
| 4,812,985 A | 3/1989 | Hambrick | | 700/215 |
| 4,817,050 A | 3/1989 | Komatsu et al. | | 707/10 |
| 4,835,372 A | 5/1989 | Gombrich | | 235/375 |
| 4,850,009 A | 7/1989 | Zook et al. | | 379/93.17 |
| 4,885,571 A | 12/1989 | Pauley et al. | | 340/573.4 |
| 4,898,578 A | 2/1990 | Rubalcaba, Jr. | | 604/66 |
| 4,911,327 A | 3/1990 | Shepherd | | 368/10 |
| 4,916,441 A | 4/1990 | Gombrich | | 345/169 |
| 4,952,928 A | 8/1990 | Carroll et al. | | 340/10.41 |
| 4,967,928 A | 11/1990 | Carter | | 221/2 |
| 4,971,221 A | 11/1990 | Urquhart | | 368/10 |
| 4,973,944 A | 11/1990 | Maletta | | 340/568.1 |
| 4,978,335 A | 12/1990 | Arthur, III | | 604/67 |
| 4,980,671 A | 12/1990 | McCurdy | | 340/568.1 |
| 5,012,229 A | 4/1991 | Lennon et al. | | 345/1.1 |
| 5,014,798 A * | 5/1991 | Glynn | | 177/25.19 |
| 5,014,875 A * | 5/1991 | McLaughlin et al. | | 221/2 |
| 5,032,823 A | 7/1991 | Bower et al. | | 340/572.8 |
| 5,038,023 A | 8/1991 | Saliga | | 235/385 |
| 5,048,870 A | 9/1991 | Mangini et al. | | 283/81 |
| 5,071,168 A | 12/1991 | Shamos | | 283/117 |
| 5,075,670 A | 12/1991 | Bower et al. | | 340/573.4 |
| 5,078,683 A | 1/1992 | Sancoff et al. | | 604/67 |
| 5,099,463 A * | 3/1992 | Lloyd et al. | | 368/10 |
| 5,104,374 A | 4/1992 | Bishko et al. | | 604/31 |
| 5,115,223 A | 5/1992 | Moody | | 340/573.1 |
| 5,142,484 A * | 8/1992 | Kaufman et al. | | 222/638 |
| 5,161,199 A | 11/1992 | David | | 704/201 |
| 5,164,575 A | 11/1992 | Neeley | | 235/472.01 |
| 5,166,498 A | 11/1992 | Neeley | | 235/375 |
| 5,176,285 A | 1/1993 | Shaw | | 221/3 |
| 5,181,189 A * | 1/1993 | Hafner | | 368/10 |
| 5,193,855 A | 3/1993 | Shamos | | 283/117 |
| 5,202,929 A | 4/1993 | Lemelson | | 382/116 |
| 5,204,670 A | 4/1993 | Stinton | | 340/10.5 |
| 5,230,441 A * | 7/1993 | Kaufman et al. | | 221/25 |
| 5,256,157 A | 10/1993 | Samiotes et al. | | 604/246 |
| 5,287,414 A | 2/1994 | Foster | | 382/100 |
| 5,289,157 A | 2/1994 | Rudick | | 368/10 |
| 5,303,214 A | 4/1994 | Kulakowski | | 369/30.3 |
| 5,313,052 A | 5/1994 | Watanabe | | 235/375 |
| 5,317,506 A | 5/1994 | Coutre et al. | | 604/65 |
| 5,319,363 A | 6/1994 | Welch et al. | | 340/825.36 |
| 5,319,711 A | 6/1994 | Servi | | 380/247 |
| 5,337,919 A | 8/1994 | Spaulding | | 221/2 |
| 5,348,061 A | 9/1994 | Riley | | 141/104 |
| 5,377,864 A * | 1/1995 | Blechl et al. | | 221/2 |
| 5,381,487 A | 1/1995 | Shamos | | 382/115 |
| 5,398,220 A | 3/1995 | Barker | | 369/29.02 |
| 5,408,443 A * | 4/1995 | Weinberger | | 368/10 |
| 5,408,655 A | 4/1995 | Oren et al. | | 715/501.1 |
| 5,431,299 A | 7/1995 | Brewer | | 221/2 |
| 5,442,728 A * | 8/1995 | Kaufman et al. | | 704/270 |
| 5,445,621 A | 8/1995 | Poli et al. | | 604/246 |
| 5,455,851 A | 10/1995 | Chaco et al. | | 379/38 |
| 5,477,511 A | 12/1995 | Englehardt | | 369/25.01 |
| 5,478,991 A | 12/1995 | Watanabe | | 235/375 |
| 5,491,482 A | 2/1996 | Dingwall et al. | | 342/42 |
| 5,491,774 A | 2/1996 | Norris et al. | | 704/270 |
| 5,493,805 A | 2/1996 | Penuela et al. | | 40/633 |
| 5,499,626 A | 3/1996 | Willham et al. | | 600/300 |
| 5,502,445 A | 3/1996 | Dingwall et al. | | 342/51 |
| 5,504,474 A | 4/1996 | Libman et al. | | 340/573.4 |
| 5,511,000 A | 4/1996 | Kaloi et al. | | 704/201 |
| 5,512,879 A | 4/1996 | Stokes | | 340/573.4 |
| 5,512,880 A | 4/1996 | Abrams et al. | | 340/573.4 |
| 5,519,808 A | 5/1996 | Benton, Jr. et al. | | 704/270 |
| 5,522,525 A * | 6/1996 | McLaughlin et al. | | 221/4 |
| 5,525,969 A | 6/1996 | LaDue | | 340/573.4 |
| 5,527,289 A | 6/1996 | Foster et al. | | 604/151 |
| 5,532,705 A | 7/1996 | Hama | | 343/718 |
| 5,541,580 A | 7/1996 | Gerston et al. | | 340/573.4 |
| 5,541,583 A | 7/1996 | Mandelbaum | | 340/10.51 |
| 5,548,566 A | 8/1996 | Barker | | 369/29.02 |
| 5,548,660 A | 8/1996 | Lemelson | | 38/116 |
| 5,551,822 A * | 9/1996 | Pippin et al. | | 414/273 |
| 5,564,005 A | 10/1996 | Weber et al. | | 345/863 |
| 5,593,267 A | 1/1997 | McDonald | | 414/273 |
| 5,594,786 A | 1/1997 | Chaco et al. | | 379/93.09 |
| 5,609,268 A | 3/1997 | Shaw | | 221/2 |
| 5,609,716 A | 3/1997 | Mosher, Jr. | | 156/522 |
| 5,612,675 A | 3/1997 | Jennings et al. | | 340/573.1 |
| 5,621,384 A | 4/1997 | Crimmins et al. | | 340/539 |
| 5,623,242 A | 4/1997 | Dawson | | 340/311.1 |
| 5,627,520 A | 5/1997 | Grubbs et al. | | 340/572.1 |
| 5,629,981 A | 5/1997 | Nerlikar | | 713/168 |
| 5,642,906 A | 7/1997 | Foote et al. | | 283/67 |
| 5,643,212 A | 7/1997 | Coutre | | 604/131 |
| 5,646,912 A * | 7/1997 | Cousin | | 368/10 |
| 5,650,766 A | 7/1997 | Burgmann | | 340/539 |
| 5,657,236 A * | 8/1997 | Conkright | | 700/244 |
| 5,659,741 A | 8/1997 | Eberhardt | | 707/104.1 |
| 5,660,176 A | 8/1997 | Iliff | | 600/300 |
| 5,671,362 A | 9/1997 | Cowe | | 705/28 |
| 5,678,925 A | 10/1997 | Garmaise | | 374/157 |
| 5,681,285 A | 10/1997 | Ford et al. | | 604/151 |
| 5,689,567 A | 11/1997 | Miyauchi | | 713/176 |
| 5,713,856 A | 2/1998 | Eggers et al. | | 604/65 |
| RE35,743 E | 3/1998 | Pearson | | 221/2 |
| 5,732,401 A | 3/1998 | Conway | | 705/29 |
| 5,742,233 A | 4/1998 | Hoffman et al. | | 340/573.1 |
| 5,768,813 A | 6/1998 | Reboul et al. | | 40/301 |
| 5,771,001 A | 6/1998 | Cobb | | 340/573.1 |
| 5,772,635 A | 6/1998 | Dastur et al. | | 604/131 |
| 5,781,442 A | 7/1998 | Engleson et al. | | 364/478.02 |
| 5,782,805 A | 7/1998 | Meinzer et al. | | 604/131 |
| 5,793,290 A | 8/1998 | Eagleson et al. | | 340/573.4 |
| 5,839,836 A | 11/1998 | Yuyama et al. | | 400/62 |
| 5,851,186 A | 12/1998 | Wood et al. | | 600/437 |
| 5,855,395 A | 1/1999 | Foote et al. | | 283/67 |
| 5,868,135 A * | 2/1999 | Kaufman et al. | | 600/300 |
| 5,868,669 A | 2/1999 | Iliff | | 600/300 |
| 5,877,675 A | 3/1999 | Rebstock et al. | | 340/286.07 |
| 5,877,742 A | 3/1999 | Klink | | 345/685 |
| 5,882,338 A | 3/1999 | Gray | | 604/131 |
| 5,883,370 A | 3/1999 | Walker et al. | | 235/375 |
| 5,883,576 A | 3/1999 | De La Huerga | | 340/573.1 |
| 5,883,806 A * | 3/1999 | Meador et al. | | 700/244 |
| 5,924,074 A | 7/1999 | Evans | | 705/3 |
| 5,936,529 A | 8/1999 | Reisman et al. | | 340/573.1 |
| 5,954,700 A | 9/1999 | Kovelman | | 604/232 |
| 5,960,085 A | 9/1999 | de la Huerga | | 340/5.61 |
| 5,970,388 A | 10/1999 | Will | | 340/7.29 |
| 5,979,757 A | 11/1999 | Tracy et al. | | 235/383 |
| 5,980,501 A | 11/1999 | Gray | | 604/408 |
| 5,988,858 A * | 11/1999 | Yuyama et al. | | 700/230 |
| 5,997,476 A | 12/1999 | Brown | | 600/300 |
| 6,019,745 A | 2/2000 | Gray | | 604/131 |
| 6,036,231 A | 3/2000 | Foote et al. | | 283/67 |
| 6,070,148 A | 5/2000 | Mori et al. | | 705/26 |
| 6,070,761 A | 6/2000 | Bloom et al. | | 222/81 |
| 6,075,755 A * | 6/2000 | Zarchan | | 368/10 |
| 6,104,295 A | 8/2000 | Gaisser et al. | | 340/573.4 |
| 6,110,152 A | 8/2000 | Kovelman | | 604/232 |
| 6,140,936 A | 10/2000 | Armstrong | | 340/5.74 |

| | | | |
|---|---|---|---|
| 6,144,303 A | 11/2000 | Federman | 340/573.4 |
| 6,255,951 B1 | 7/2001 | De La Huerga | 340/573.1 |
| 6,263,330 B1 | 7/2001 | Bessette | 707/4 |
| 6,294,999 B1 | 9/2001 | Yarin | 340/573.1 |
| 6,308,109 B1 * | 10/2001 | Yuyama et al. | 700/228 |
| 6,346,886 B1 | 2/2002 | De La Huerga | 340/573.1 |
| 6,601,729 B1 * | 8/2003 | Papp | 221/25 |
| 6,745,941 B1 | 6/2004 | Vega | 235/382 |

FOREIGN PATENT DOCUMENTS

| | | |
|---|---|---|
| GB | 2154344 | 9/1985 |
| WO | WO01/93801 A1 * | 12/2001 |

\* cited by examiner

| | |
|---|---|
| 119 | Medication Information From Pharmaceutical Manufacturer On Electric Label 118 of Bulk Container 110 |
| 119a | Pharmaceutical Manufacturer Supplied Information<br>Medication Name<br>Quantity Initially in Container<br>Quantity Remaining in Container<br>Expiration Date for the Medication<br>Medication Lot Code<br>Special Instruction for Consuming the Medication; e.g. Before or After Meals<br>List of Contraindicated Medications |
| 119b | After Dispensing or Refilling<br>Identification of Healthcare Worker Dispensing/Refilling Medication<br>Date & Time Medcation Dispensed/Refilled |

Fig. 6

| | |
|---|---|
| 109 | Medication Information Written to Information Strip 100, 240, 460 of Medication Cassette 10, 300, or 400 |
| 109a | Prior to Filling Cassette with Medication<br>Identification Number<br>Encryption Codes<br>Battery Life<br>Cassette History/Past Use Information |
| 109b | After Filling Cassette with Medication<br>Medication Name, per Compartment 50, Pocket 415, Unit Dose Blister 350<br>Quantity of Medication in Cassette<br>Expiration Date for the Medication<br>Medication Lot Code<br>Special Instruction for Consuming the Medication; e.g. Before or After Meals<br>List of Contraindicated Medications<br>Date and Time Medication Dispensed into Cassette<br>Identification of Healthcare Worker Who dispensed Medication into Cassette<br>Date and Time Medication Dispensed into Cassette |
| 109c | After Dispensing Medication to Portable Container 190<br>Identification of Healthcare Worker Who Dispensed Medication into Portable Container<br>Identification of Patient for Whom Medication is Dispensed<br>Date and Time Medication Dispensed into Portable Container |

Fig. 9

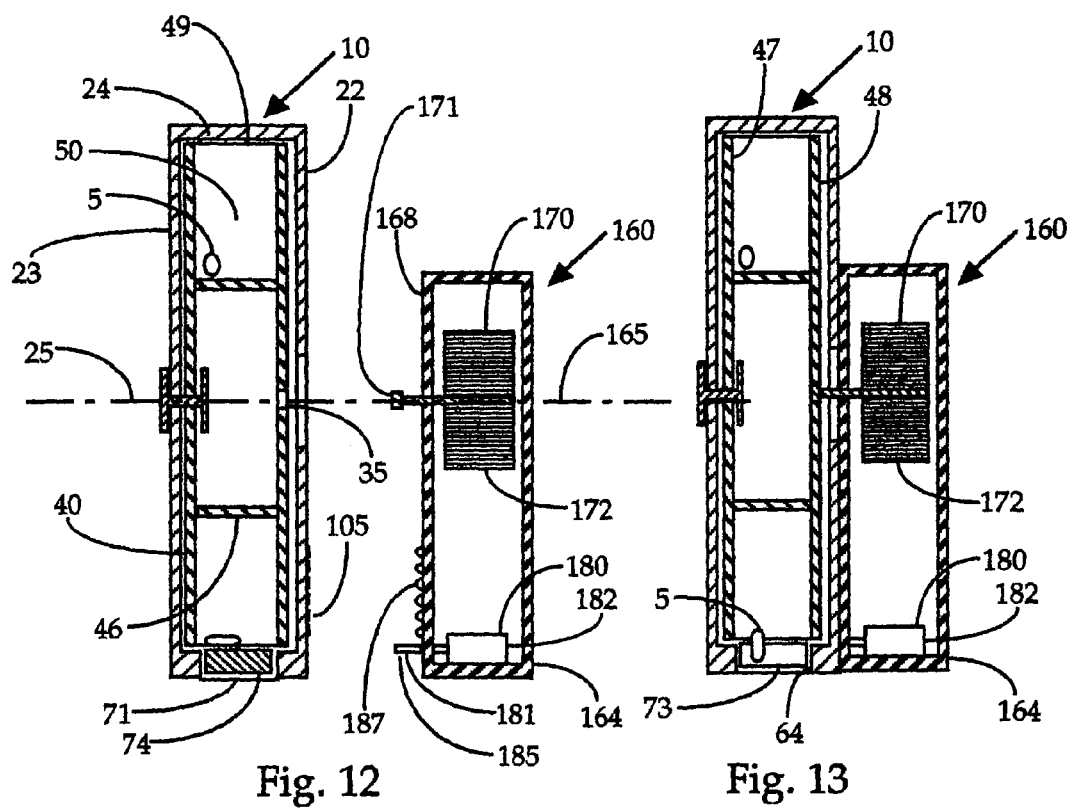

| | |
|---|---|
| 199 | Medication Information -- Written to Information Device 195 of Portable Container 190 |
| 199a | Prior to Filling Portable Container with Medication<br>　　Identification Number<br>　　Encryption Codes<br>　　Battery Life<br>　　Container History / Past Use Information |
| 199b | After Filling Container with Medication<br>Predetermined Patient Information for Dispensed Medication<br>　　Patient Identification Number<br>　　Patient Name<br>　　Patient Room Number<br><br>Selected Prescribed Medication Dose Information for each Medication Prescribed<br>　　Medication Type Prescribed<br>　　Medication Quantity Prescribed<br>　　Dosing Times<br>　　Identification of Physician Prescribing Medication<br><br>Healthcare Worker Information Who Dispensed Medication |
| 199c | After Administering Medication to Patient<br>Specific Patient Information<br>　　Patient Identification Number<br>　　Patient Name<br>　　List of Medications to which Patient is Allergic<br>　　Admitting Physician<br>　　Patient Blood Type<br><br>Administering Healthcare Worker Information<br>　　Responsibilities / Title<br>　　Identification Number<br>　　Name<br>　　List of Patients Under Care of Healthcare Worker<br><br>Consumption Information:<br>　　Consumption Tiem Information / Date and time portable container opened<br>　　Amount of Medication offered to Patient<br>　　Amount of Medication Patient Consumed<br><br>Medication Report |

Fig. 14

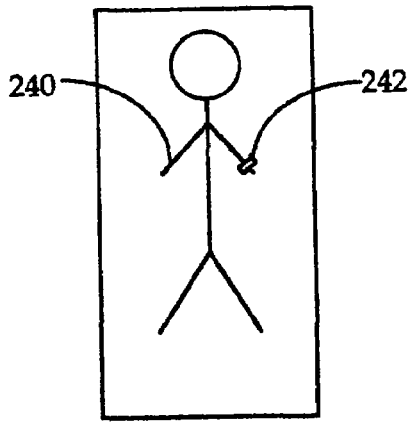

Fig. 15

| 249 | Memory Contents -- Wrist Band 242 of Patient 240 |
|---|---|
| | Specific Patient Information<br>    Patient Identification Number<br>    Patient Name<br>    List of Medications to Which Patient is Allergic |

Fig. 16

| 229 | Memory Contents -- Hospital or Pharmacy Database 222, 224 |
|---|---|
| | Prescription Data<br>    Patient Information<br>        Patient Name<br>        Patient Identification Number<br>        Patient Room Number<br>    Physician Medication Order<br>        Prescribed Medication Name<br>        Prescribed Medication Dosing Quantity<br>        Prescribed Medication Dosing Times<br>        Prescription Order Number |
| | Medication Administration Data<br>    When Medication Administered<br>    Healthcare Worker Who Administered Medication<br>    Medication and Quantity Administered |
| | Inventory Information<br>    Pharmacy Inventory Including Each Bulk Container<br>    Individual Hospital Floor Dispensing Machine Inventory<br>        Including Each Cassette and Portable Container<br>    Comprehensive Total Inventory for Entire Hospital and<br>        Phramacy |

Fig. 17

INTERACTIVE MEDICATION CASSETTE

CROSS-REFERENCE TO RELATED APPLICATIONS

This divisional application is related to prior application Ser. No. 09/168,783, filed on Oct. 8, 1998, now U.S. Pat. No. 6,611,733, issued on Aug. 26, 2003 for Interactive Medication Dispensing Machine, which claims benefit of Provisional Application Ser. No. 60/096,269, filed on Aug. 12, 1998 and is a Continuation-In-Part of Ser. No. 08/955,475 filed on Oct. 21, 1997, now U.S. Pat. No. 6,032,155, and which is also a Continuation-In-Part of Ser. No. 08/832,613 filed on Mar. 28, 1997, now U.S. Pat. No. 5,852,590 which claims benefit of Provisional Application Ser. No. 60/033,491 filed on Dec. 20, 1996.

TECHNICAL FIELD

This invention pertains to a medication cassette with an interactive information strip used in a hospital medication distribution and inventory system that includes medication dispensing machines located throughout the hospital, and a process of using the cassette to improve the flow of information about and control the access to the medication during the distribution process.

BACKGROUND

The use of containers in medication dispensing machines is well known. Examples of containers used in such automated machines are disclosed in U.S. Pat. Nos. 4,674,652 (Aten); U.S. Pat. No. 4,823,982 (Aten); U.S. Pat. No. 5,213,232 (Kraft); U.S. Pat. No. 5,401,059 (Ferrario); U.S. Pat. No. 5,405,048 (Rogers); U.S. Pat. No. 5,431,299 (Brewer); U.S. Pat. No. 5,502,944 (Kraft); U.S. Pat. No. 5,508,499 (Ferrario) and U.S. Pat. No. 5,522,525 (McLaughlin). Various types of dispensing machines are also known in the medication dispensing art, such as U.S. Pat. Nos. 5,468,110 (McDonald) and 5,593,269 (McDonald), the disclosures of which are incorporated by reference. Many of these containers and dispensing machines are designed for use in hospitals and other healthcare facilities.

A problem with conventional medication containers is integrating them into an automated hospital or healthcare medication distribution and inventory or information system. The problem is further complicated when the system is designed to maintain control over the access to the medication. For example, in a hospital, medication is typically ordered and received by the hospital pharmacy. The pharmacy orders and receives most types of medication from pharmaceutical manufacturers in bulk medication containers containing a large quantity of the medication. The hospital pharmacy maintains control over these bulk containers by limiting the access to them to specific hospital personnel such as licensed pharmacists and their support staff, Entry into the hospital pharmacy is restricted to these personnel.

A distribution problem arises because the hospital pharmacy is located in one part of the hospital while patients are located throughout the many floors and wings of the hospital. The larger the hospital or healthcare facility, the greater the distribution problem becomes. If all medication were kept in the hospital pharmacy, healthcare workers such as nurses and physicians would have to make numerous trips to and from the pharmacy throughout the day to obtain medication for their patients. Because this is impractical, most hospital medication distribution systems include a variety of sites or rooms for storing and dispensing medication throughout the hospital. For example, the intensive care unit requires a small quantity of a wide variety of medications to be stored in its medication dispensing room. In emergency situations, there is no time to walk to the other end of the hospital and negotiate the stairwells and elevators to obtain a specific medication.

Maintaining adequate inventories of hundreds or thousands of medications, tracking the flow of these medication through a hospital or healthcare facility, controlling the access to the powerful and expensive medications kept at the dispensing sites, and organizing and storing these medications so that they can be easily identified and obtained during normal and emergency situations is no easy task. The more control over the access to the medication, the more cumbersome it is for the healthcare workers to efficiently perform their jobs and administer the prescribed medications to their patients. To facilitate the ease and efficiency of performing their jobs, healthcare workers are frequently allowed easy access to many medications kept in their area of the hospital. This efficiency comes at a price. The ease of access to the medication compromises the pharmacy's control over the medication distribution and inventory system. The pharmacy has a difficult time identifying which medications are running low. In addition, medication is more easily misplaced, lost or stolen by healthcare workers, patients, hospital staff and visitors. This situation becomes more problematic each year as more and more powerful and expensive drugs are introduced into hospital medication distribution and inventory systems.

To improve control over the medication distribution and inventory system, many hospitals are using automated or semi-automated medication dispensing machines at various medication distribution sites throughout the hospital. The dispensing machines usually include a computer processor and keyboard for communicating with the machine. These automated dispensing machines are often designed to improve control over the medication kept inside them by requiring healthcare workers to identify themselves or a specific patient before the machines will dispense a dose of medication. The machines frequently contain several smaller medication containers or cassettes that each hold a specific type of medication. The cassettes may be removed from the dispensing machine to fill with a desired type and quantity of medication, but may be locked or otherwise stored inside the dispensing machine during use.

Several problems remain in conventional medication distribution and inventory systems using automated medication dispensing machines. One problem is that the dispensing machine cassettes do not keep track of the quantity of medication doses they contain. The cassettes are not designed to keep track of the type and amount of medication they contain during use, and do not communicate this information to the dispensing machine. In order to tell how much medication is left in a particular container it is frequently necessary to open it up and count the doses it contains. Systems that require healthcare workers to open the cassettes on the hospital floor can be cumbersome to use and diminish the control over the access to the medication outside of the pharmacy.

These systems also suffer from the problem that it is difficult for healthcare workers to tell when the dispensing machines are running out of a specific type of medication. If improved access control is desired, the dispensing machines have to be locked. One of the pharmacy staff has to do rounds on a regular basis to ensure the dispensing machines are properly stocked and to add additional doses of medication to the cassettes when needed. This is a time consuming and monotonous job that is prone to mistakes.

Another problem with automated dispensing machines is that in order to maintain control over the access to medication, the pharmacy staff is burdened with the task of inserting the cassette into the dispensing machine and manually entering medication quantity information into the machine. Again, this data entry process is a time consuming and monotonous job that is prone to mistakes that prevent accurate tracking of medication in the distribution and inventory system. In addition, pharmacy personnel are frequently performing other jobs that prevent them from refilling the cassettes and delivering them to the necessary distribution machines when needed.

Another problem is that the cassettes are not able to communicate with the bulk containers in the hospital pharmacy. When an unused quantity of medication is taken from the cassettes and returned to the bulk containers, the doses of medication must be counted by the pharmacy staff before adding them back to the bulk container. The bulk container must then be updated to reflect the appropriate increase in medication in the bulk container. This is yet another monotonous task that is prone to mistakes that render the medication inventory system unreliable. In addition, no mechanism is provided to ensure that the pharmacy staff returns the medication to the proper bulk container.

A similar problem arises when a patient is prescribed a special type of medication that is kept in only one or two of the various medication dispensing machines. When the patient is moved from one area of the hospital to another, such as from intensive care to surgery, the cassette containing the special medication must be removed from one dispensing machine and placed in another located closer to the patient. Unfortunately, conventional dispensing machines and cassettes are not provided with a mechanism for communicating updated quantity information when a cassette is transferred from one dispensing machine to another. Instead, a healthcare worker or one of the pharmacy personnel must count the number of doses remaining in the cassette to ensure there is an adequate amount remaining before loading the cassette in the other dispensing machine and manually entering this quantity information in new dispensing machine.

Another problem with conventional medication cassettes is that they are not capable of easily facilitating a pharmaceutical manufacturer recall of a specific batch of medication. Once medication is dispensed from a bulk medication container, the pharmacist has difficulty locating, identifying and gathering up the medication should the manufacturer recall the batch of medication. A similar problem occurs for medication that has a predetermined shelf life. Once the shelf life has been exceeded, the pharmacist has difficulty locating, identifying and gathering up the expired medication.

Another problem with conventional medication cassettes is that they are not designed to help maintain control over the access to the medication in the cassette after it leaves the pharmacy or is inserted into a dispensing machine. Many conventional cassettes are not sealed to prevent access to the medication inside. Other conventional cassettes are sealed but not locked shut. This creates an undesirable situation given the powerful nature of many new drugs and the cost of these drugs.

Another problem with conventional dispensing machine cassettes is that they do not keep track of the physician that prescribed the medication, the health care worker that dispensed the medication or the patient for whom the medication was dispensed. When the pharmacist pulls the cassette from the dispensing machine or the cassette is returned to the hospital pharmacy, the cassette does not contain information about the prescribing physician, the administering healthcare worker or the patient that was given the medication. This information is often desirable to the pharmacist as a double check to ensure that the medication was given to the correct patient by an authorized healthcare worker.

Another problem with conventional dispensing machine cassettes is that they are not designed to be readily integrated into a comprehensive distribution and inventory database system. The hospital staff must determine the type and quality of medication in each cassette for every dispensing machine located throughout the hospital. This information must then be added to the pharmacy data base to obtain a comprehensive inventory for the hospital.

The present invention helps overcome these and other limitations in cassettes used in conventional hospital medication distribution and inventory systems.

SUMMARY OF THE INVENTION

This invention relates to an interactive medication cassette with a machine readable and writable information strip that contains information corresponding to the medication in the cassette. The interactive medication cassette holds the medication and couples the corresponding information to the medication. The cassette is designed for use in a medication distribution and inventory system that includes at least one medication dispensing machine having a sensor for reading the information in the strip and updating or altering this information when medication is added to or removed from the cassette. The cassette travels with the medication during the distribution of the medication to a patient, and its information is reported to one or more memory devices or hospital or pharmacy data bases during this process. The cassette is filled by a pharmacy dispensing machine holding a bulk container filled with a particular type of medication and a singulator for counting the quantity of medication added to the cassette. The pharmacy dispensing machine alters the information strip to include medication information and quantity information corresponding to the dispensed medication. The cassette is closed and locked to prevent unauthorized access during transport to a hospital floor workstation. A hospital floor dispensing machine incrementally dispense the medication from the cassette, and updates the information strip with additional information including the quantity of medication dispensed from the cassette. When the cassette is returned to the pharmacy and its unused contents is emptied into the bulk container, the information strip on the cassette automatically updates an information strip on the bulk container to indicate the number of doses of medication added to the bulk container. In this manner, a reliable medication distribution and inventory system is achieved while maintaining improved control over the access to the medication on the hospital floor.

A main advantage of the present cassette is that it keeps track of the type and quantity of medication doses it contains during use on the hospital floors and in the dispensing machines. The information strip contains information pertaining to both the type and quantity of medication it contains during use. This information can be easily communicated to the dispensing machine and displayed to a healthcare worker. The healthcare worker does not have to open the dispensing machine or the cassette to determine the types and quantities of medication it contains. Accordingly, the cassette improves the flow of information and the control over the access to the medication during distribution on the hospital floor.

Another advantage of the present invention is that the cassette is designed to lock into a closed position during transportation to and from the pharmacy or another dispensing machine. The medication in the cassette is not easily accessible during use. Medication is not dispensed from the cassette by a dispensing machine until after the healthcare worker identifies themselves and the patient for whom the medication has been prescribed. Even then, the medication is dispensed and locked in a portable container for transport to the patient. Only after the portable container reaches the correct patient can a healthcare worker gain access to the medication in the portable container. This is important given the powerful nature of many new drugs and the cost of these drugs.

Another advantage of the present invention is that the cassette enables the dispensing machines and healthcare workers to easily tell when a machine is running low or is out of a specific type of medication. The dispensing machines can read the amount of medication remaining in each of its cassettes and activate an alarm or display if a cassette falls below a predetermined level or is empty. This is accomplished without opening the machine and compromising medication access control. Nor is it necessary for pharmacy staff to spend the time and effort of making regular rounds to ensure the dispensing machines are properly filled.

Another advantage of the present invention is that it provides the flexibility of allowing healthcare workers to come to the pharmacy and pick up the cassettes they need at a convenient time. After inserting the cassette into their dispensing machine, the quantity of medication will automatically be read by the dispensing machine and communicated to the healthcare worker when requested or when necessary. The pharmacy staff is not burdened with the mandatory task of taking cassettes to the appropriate dispensing machines throughout the hospital, inserting one or more cassettes into each machine and manually entering medication quantity information into the machines.

Another advantage of the present invention is that the cassettes are capable of communicating with the bulk containers in the hospital pharmacy. When an unused quantity of medication is taken from the cassettes and returned to the bulk container, the information strip on the cassette is read by an associated pharmacy computer system and communicated to the bulk container to indicate that the quantity of medication in the bulk container has been increased by the amount of unused doses of medication in the cassette. The doses of medication need not be counted by the pharmacy staff before adding them back to the bulk container. The bulk container is automatically updated to reflect the appropriate increase in medication in the bulk container. In addition, the information strip of the cassette is checked to ensure that its contents is being added to the appropriate bulk container. An alarm will activate if the type of medication in the cassette does not match the type of medication in the bulk container.

The present invention provides a similar advantage when a patient is prescribed a special type of medication that is kept in only one or two medication dispensing machines. When the patient is moved from one area of the hospital to another, the cassette containing the special medication can be easily sealed and locked by the dispensing machine control system prior to removal. The locked cassette is then placed in another dispensing machine located closer to the new location of the patient without compromising access control. The information strip in the cassette is updated or altered by the first dispensing machine to subtract out the quantity of medication already dispensed. When the cassette is inserted in the other dispensing machine, the actual remaining quantity of medication in the cassette is communicated to the other dispensing machine. The healthcare worker and pharmacy staff do not have to count the number of doses remaining in the cassette to ensure there is an adequate amount remaining before loading the cassette in the other dispensing machine. The healthcare worker is also saved the task of manually entering this quantity information in the other dispensing machine.

Another advantage of the present invention is that the cassettes can be easily recalled by the pharmacy. The bulk containers contain manufacturer lot and batch information that is transferred to the information strips of the cassettes. The dispensing machines are hooked up to a hospital information network and data base system that enables the pharmacy staff to identify each machine containing a quantity of the manufacturer's recalled lot and batch of medication. Similarly, the bulk containers can transfer shelf life information to the cassettes. This allows pharmacy and healthcare workers to use the network and data base system to easily identify machines containing a quantity of medication that exceeds its shelf life. An alarm or display is activated in the dispensing machine when such an occurrence arises. Even if the dispensing machines are not hooked up to a network, or if the network is down, the pharmacy staff need only enter the recalled or expired medication type into a keyboard of the dispensing machine to determine if the machine contains any of the expired or recalled medication. The machines do not have to be opened and emptied to make this determination.

Another advantage of the present invention is that the information strips on the cassettes can keep track of the physician that prescribed the medication, the health care workers that dispensed the medication and the patient for whom the medication was dispensed. When the pharmacist pulls the cassette from the dispensing machine or the cassette is returned to the hospital pharmacy, the pharmacist can use the information in the cassette to double check to ensure that the medication was given to the correct patient by an authorized healthcare worker.

Another advantage is that each dispensing machine is linked with the pharmacy database to enable the pharmacy staff to obtain a comprehensive inventory of all types and quantities of medication in the hospital. Accordingly, the pharmacy staff can now readily determine when a particular type of medication needs to be ordered.

Other advantages and aspects of the invention will become apparent upon review of the specification, claims and drawings.

BRIEF DESCRIPTION OF THE DRAWINGS

FIG. 6 is a chart of some of the information contained in the electronic label of the bulk container when initially received at the hospital, and after medication is dispensed from or refilled into the container.

FIG. 9 is a chart of some of the information contained in the information strip of the cassette before and after being filled with medication by the pharmacy workstation, and after medication is dispensed by the hospital floor workstation.

FIG. 12 is a cross-sectional, side plan view of a cassette engaging the contacts, drive key and locking pin of it corresponding dispenser, with the shutter of the cassette in its closed position.

FIG. 13 is a cross-sectional, side plan view of a cassette locked to a dispenser, with the shutter of the cassette in its open position.

FIG. 14 is a chart showing some of the information contained in the information device of a portable container before and after medication is dispensed into the portable container, and after the medication is administered to the patient.

FIG. 15 is a top view of a patient in an assigned room with a wristband having machine readable information that identifies the patient.

FIG. 16 is a chart of some of the information contained in the machine-readable portion of the patient wristband.

FIG. 17 is a chart of some of the information contained in the hospital and pharmacy databases.

DETAILED DESCRIPTION

Figure 1:
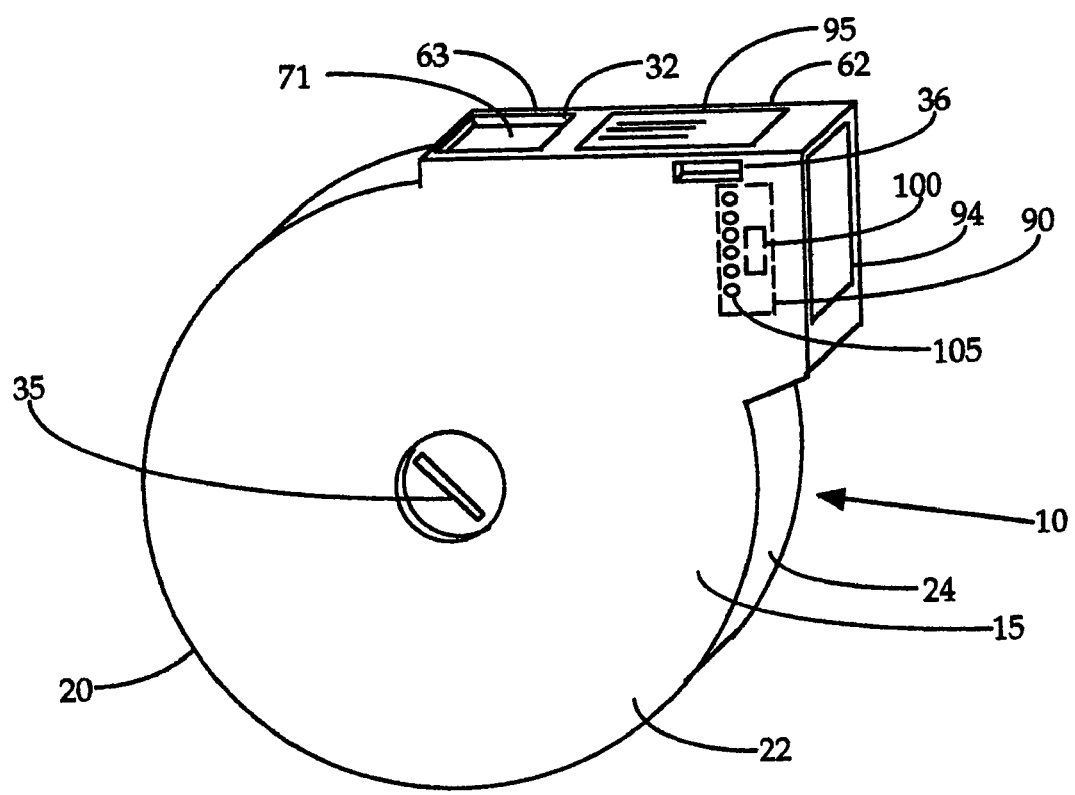
FIG. 1 is a perspective view of a first embodiment of a medication container in the form of a rotating wheel cassette having a disk shaped portion with a drive slot and a control portion with a dispensing opening, printed label, display, locking slot and electrical contacts for communicating with an internal computer processor and information strip.

The present invention relates to a medication cassette with an information strip for use in an automated medication distribution and inventory system that includes several medication dispensing machines. The cassette is particularly suited for use in a hospital medication distribution and inventory control system where improving the control over the access to the medication is important. While the invention is susceptible of embodiments in many different forms, there are shown in the drawings and will herein be described, several forms of the invention with the understanding that the present disclosure is to be considered an exemplification of the principles of the invention, and is not intended to limit the broad aspects of the invention to the several embodiments illustrated. While the invention is shown and disclosed to be particularly suited for applications in hospitals or other healthcare facilities, it should be understood that the invention is applicable for other medication dispensing purposes as well.

Figure 2:
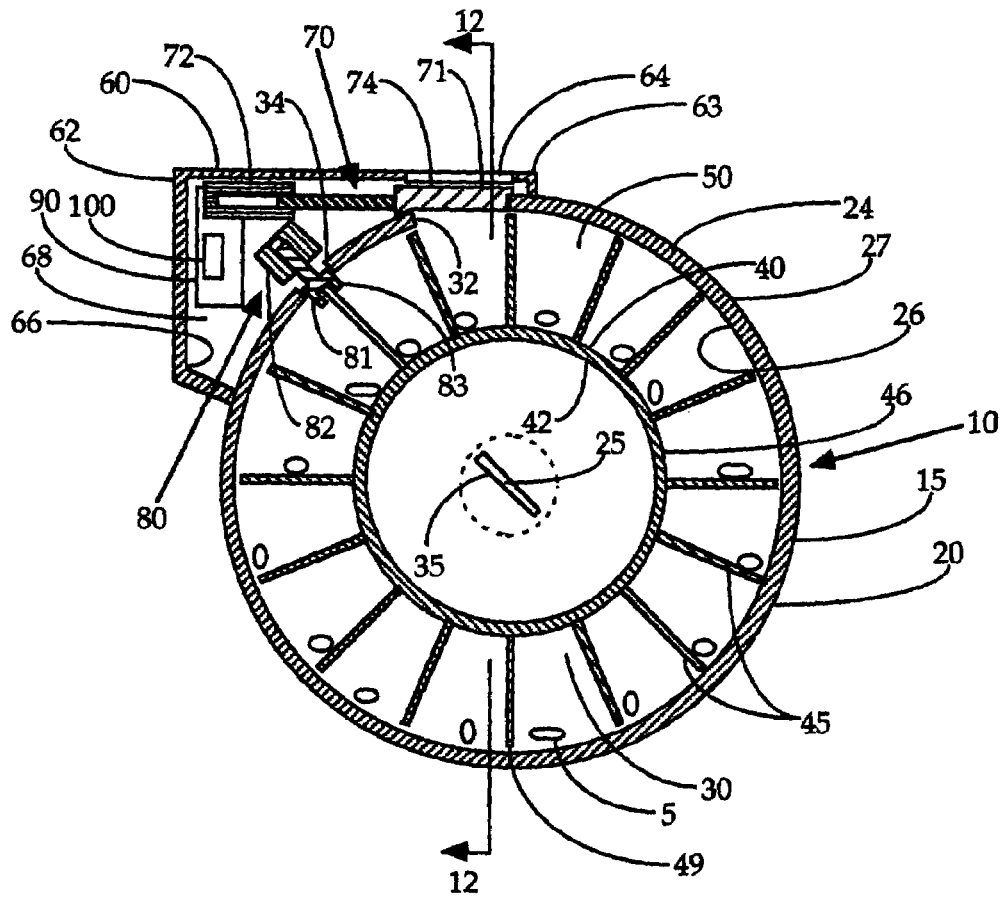
FIG. 2 is a cross sectional, plan view of the medication cassette having an internal rotating wheel that divides the cassette into a number of cells, each cell having a single dose of medication, the rotating wheel being locked in place with its shutter in a closed position.
Figure 18:
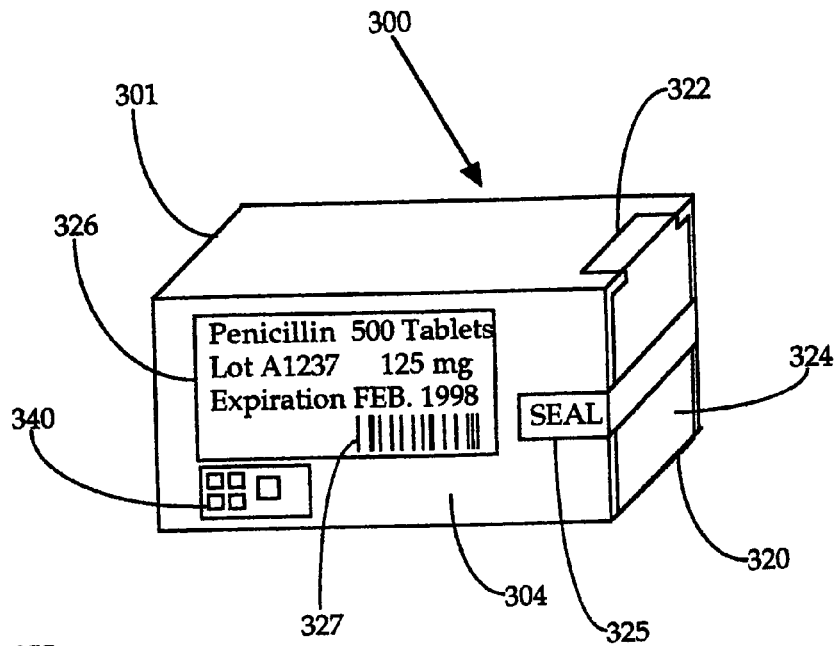
FIG. 18 is a perspective view of a second embodiment of the medication in the form of a cartridge cassette having a sealed door, a printed label and an external information strip.
Figure 19:
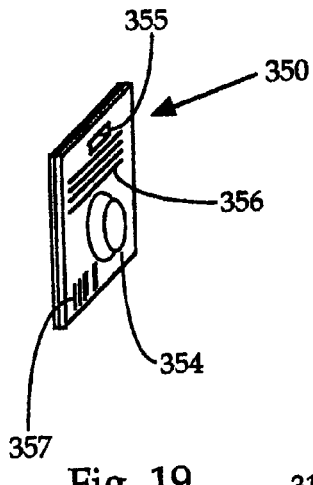
FIG. 19 is a perspective view of an individual blister pack that hangs inside the cartridge shaped cassette.
Figure 20:
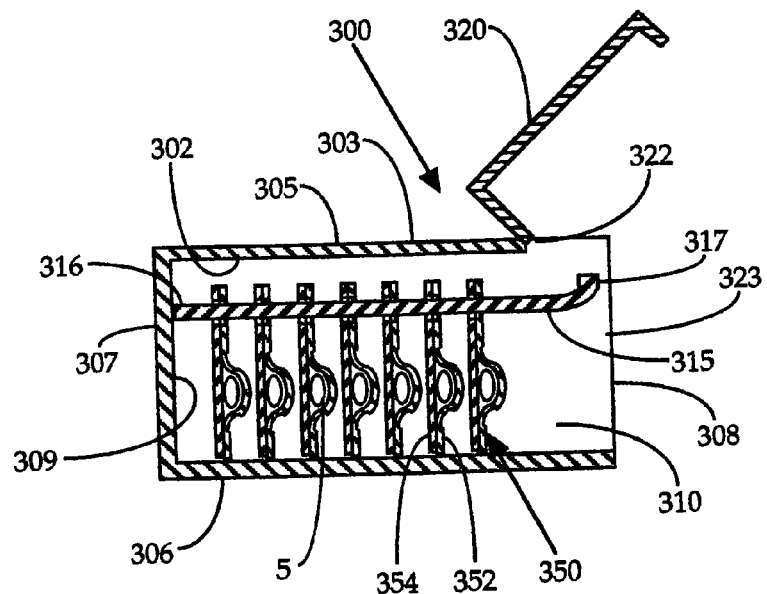
FIG. 20 is a cross-sectional, side view of the cartridge shaped cassette showing a plurality of the individual blister packs hanging inside the cartridge.
Figure 21:
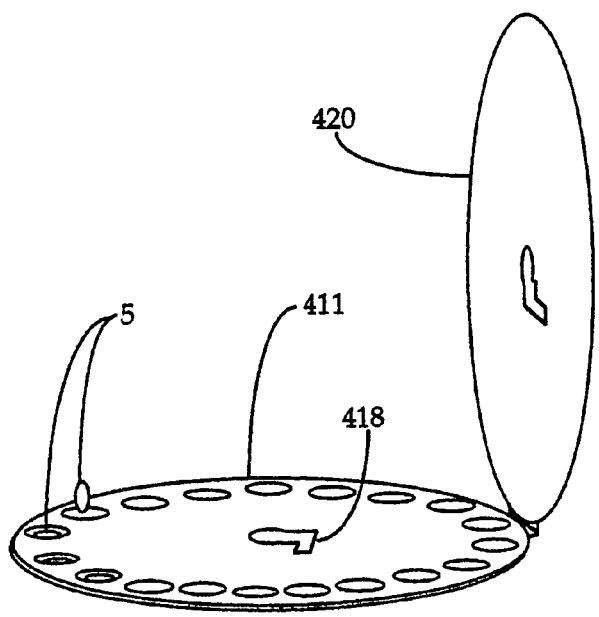
FIG. 21 is a perspective view of a third embodiment of the medication in the form of a blister pack cassette.
Figure 22:
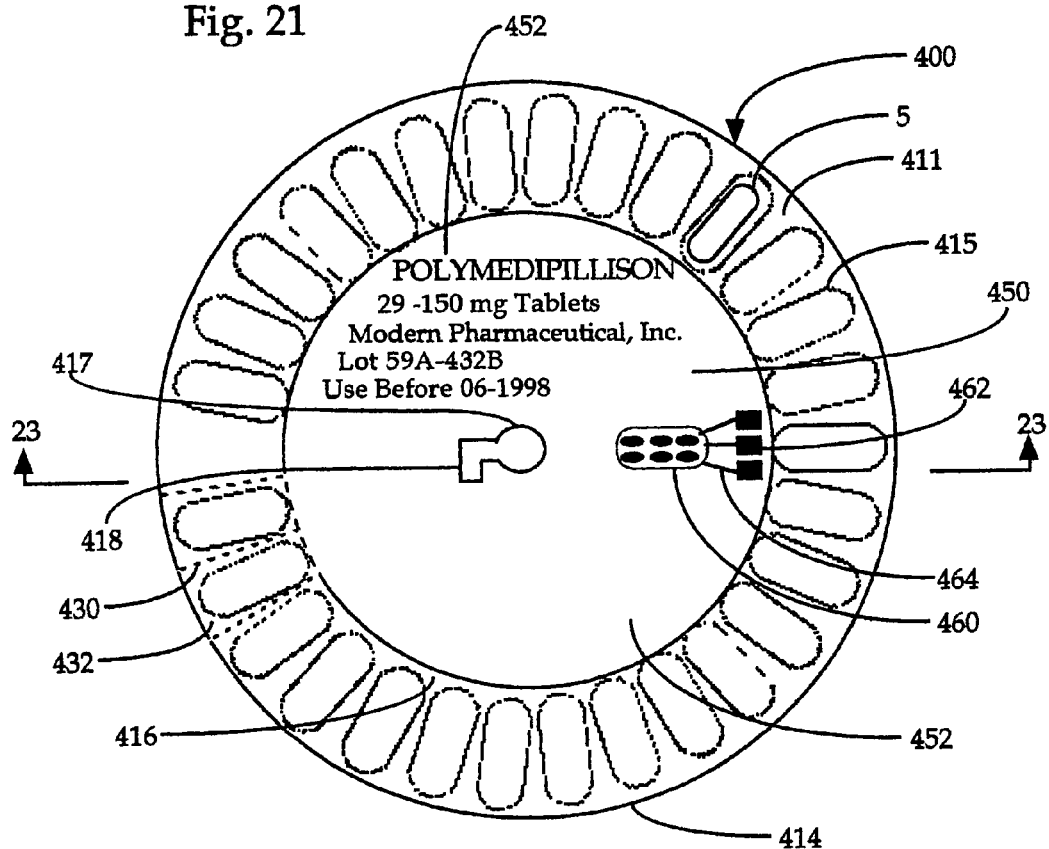
FIG. 22 is a top, plan view of the blister pack cassette having a drive slot, electrical contacts and an information strip.
Figure 23:
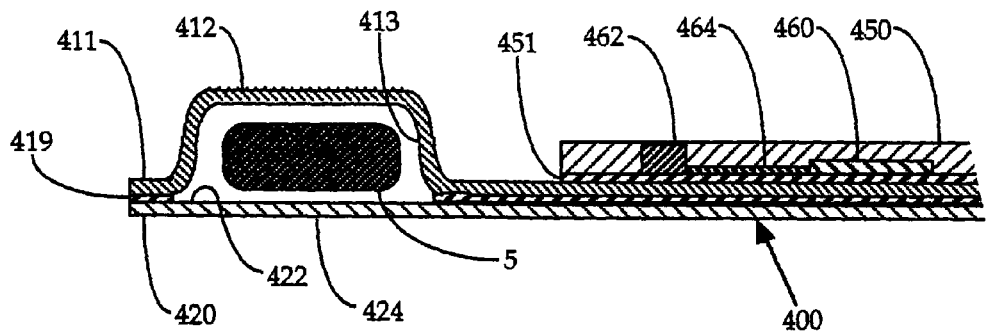
FIG. 23 is a side, plan view of the blister pack cassette showing a single dose of medication contained in a compartment of the blister pack cassette, and the information strip secured to the surface of the blister pack cassette.

The invention relates to the dispensing of medication 5 from a container or cassette 10 equipped with an interactive label or information strip 100. FIGS. 1 and 2 show the cassette 10 in a first rotating wheel embodiment. The rotating wheel cassette 10 is particularly suited for use in conjunction with a workstation 150 having a dispensing machine 151 connected to a hospital network or information system 220. However, it should be understood that the cassette 10 could take on a variety of forms without departing from the invention. For example, FIGS. 18–20 show the cassette in the form of a cartridge shaped cassette 300, while FIGS. 21–23 show the cassette in the form of a disk shaped, multi-dose blister pack cassette 400.

Rotating Wheel Cassette 10

As shown in FIGS. 1, 2, 12 and 13, the rotating wheel cassette 10 includes a housing or shell 15 that defines the outer shape of the cassette. The housing 15 is formed by an integral piece of plastic that forms two main portions of the cassette 10. The first portion is a disk shaped main body 20 that stores or holds the medication 5. The second portion is a control portion 60 that contains the controls for discharging the medication 5. The disk shaped portion 20 is formed by two spaced apart, side walls 22 and 23 that are joined together by a perimeter wall 24. The perimeter wall 24 is generally cylindrical in shape and defines a central axis 25. These walls 22–24 have inside and outside surfaces 26 and 27. The inside surface 26 defines an interior or compartment 30 for holding the medication 5. The perimeter wall 24 has a medication dispensing opening 32 that is sized and shaped to allow single doses of medication 5 to easily pass in and out of compartment 30. As discussed more fully below, the perimeter wall 24 has an aperture 34 proximal the control portion 60 for receiving a wheel locking mechanism 80. As also discussed more fully below, one or both of the side walls 22 and 23 has a drive key slot 35 located at the central axis 25 for receiving a wheel drive mechanism 170. A locking bar slot 36 is also provided for locking the cassette 10 to a dispenser 160 in the dispensing machine 151.

As best shown in FIG. 2, the compartment 30 of the disk shaped portion 20 contains an internal, rotatable wheel 40. The wheel 40 is formed by a cylindrically shaped inner wall or hub 42 located towards a center of the wheel. The hub 42 has a cylindrical outer surface 46, and a number of partitions or radially extending fins 45 that are spaced apart a uniform predetermined radial distance from each other and extend radially from an outer surface 46 of the hub. As best seen in FIGS. 12 and 13, the wheel 40 includes a pair of circular side walls 47 and 48 that form the side of the wheel. The rotating wheel 40 is sized and shaped to fit inside the disk shaped compartment 30 of the cassette 10. The rotatable wheel 40 divides the compartment 30 into a number of cells 50. Each cell 50 is formed by the outer surface 46 of the hub 42, the side walls 47 and 48 and two adjacent fins 45 of the wheel 40 and the inner surface 26 of the peripheral wall 24 of the housing 15. The hub 42 and fins 45 have a predetermined width so that the sides 47 and 48 extend close to or in sliding engagement with the inside surface 26 of the side walls 22 and 23 of the housing 15. Similarly, the fins 45 are sized so that their outer or radial end 49 extends close to or in sliding engagement with the inside surface 26 of the peripheral wall 24 of the housing 15. Medication placed in one cell 50 is not able to enter an adjacent cell 50. The radial ends 49 of two adjacent fins 45 are spaced apart a predetermined radial distance that is substantially the same size as the medication dispensing opening 32 in the peripheral wall 24.

The control portion 60 of the housing 15 is formed by an L-shaped outer wall 62 having a portion 63 that extends generally tangentially to the peripheral wall 24 of the disk shaped portion 20. The tangent portion 63 of the wall 62 is secured to and extends from a location near the opening 32 in the peripheral wall 24. The tangent portion 63 includes an opening 64 for dispensing medication that is sized and shaped substantially similar to and aligned substantially directly over the medication dispensing opening 32 in the peripheral wall 24. The wall 62 of the control portion 60 has an inside surface 66 that combines with the outside surface 27 of the peripheral wall 24 to define a compartment 68 containing the controls of the cassette 10 a such as a shutter mechanism 70, a locking mechanism 80 and a computer processor 90.

Figure 8:
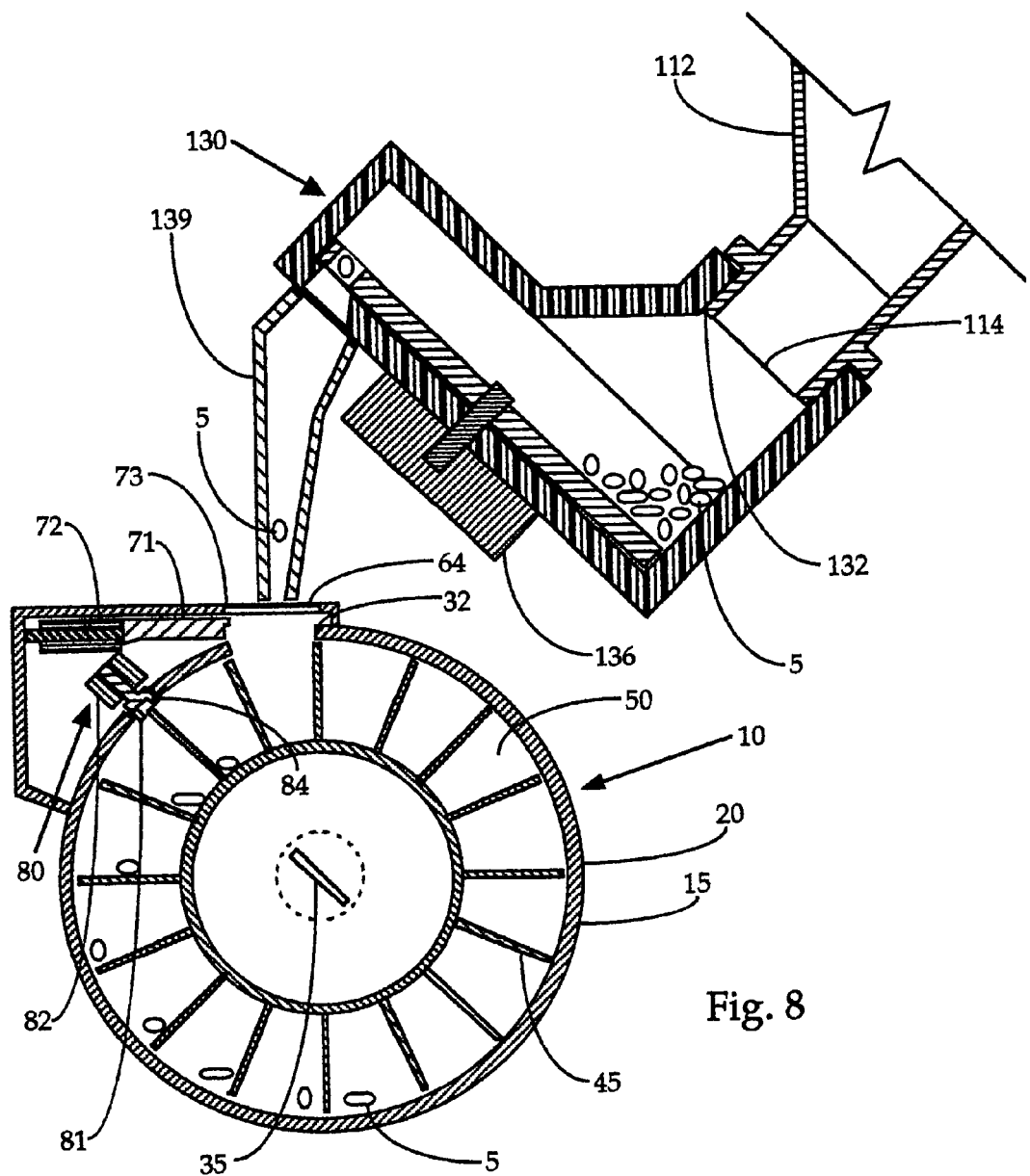
FIG. 8 is a cross sectional, side plan view showing a bulk container, singulator and cassette of a pharmacy cassette filling machine with a single dose of medication being deposited into one of the cells of the cassette.

The shutter mechanism 70 opens and closes medication dispensing openings 32 and 64. The mechanism includes a shutter 71 that extends along the inside surface 66 of and generally parallel to the tangent portion 63 of wall 62. The shutter 71 is operated by a solenoid 72 that selectively moves the shutter along the tangent portion 63 to and from open and closed positions 73 and 74 as shown in FIGS. 2 and 8. When in the closed position 74, the shutter 71 closes and seals both medication dispensing openings 32 and 64 so that the medication 5 in compartment 30 cannot be removed from the cassette 10. The solenoid 72 is biased into its closed position 74 by a spring (not shown) so that it forms a locking mechanism for locking the shutter 71 into its closed position 74 to inhibit access to the medication 5 inside the cassette 10 during transportation.

The wheel locking mechanism 80 locks the rotating wheel 40 in a given position and aligns one of the cells 50 with the dispensing openings 32 and 64. The locking mechanism 80 includes a locking pin 81 with a notched end that is selectively moved by a second solenoid 82 to and from locked and unlocked positions 83 and 84 as shown in FIGS. 2 and 8. When in the locked position 83, the locking pin 81 passes through aperture 34 in the peripheral wall 24 so that the notched end of the locking pin 81 engages and receives the radial end 49 of one of the fins 45 to prevent the wheel 40 from rotating. When in the unlocked position 84, the rod 81 is pulled away from and disengages the outer end 49 of the partition 45 to enable the wheel 40 to rotate, as discussed below. The locking mechanism 80 biases locking pin 81 into its locked position 83 to provide a second means for inhibiting access to all or most the medication 5 in the cassette 10 during transportation.

Figure 3:
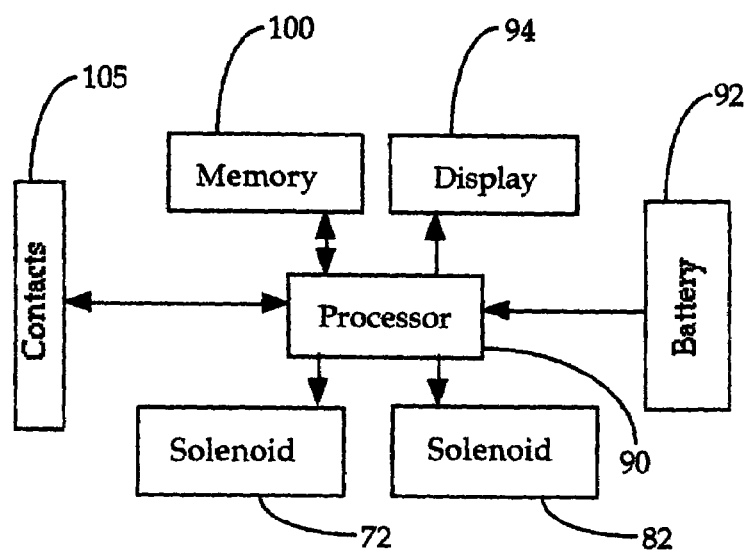
FIG. 3 is a schematic view of the circuitry of a cassette having an internal computer processor that is in electrical communication with a memory, display, battery, shutter solenoids, locking solenoid and contacts.

The computer processor 90 controls the operations of the rotating wheel cassette 10. As shown in FIG. 3, the processor 90 is electrically connected to a battery 92 and solenoids 72 and 82, and is in electrical communication with a display 94, the information strip or memory device 100, and a set of contacts 105. The battery 92 supplies power to the processor 90 which selectively transmits power to solenoids 72 and 82 and information to display 94. The display 94 is secured to the outside of the wall 62 to visually display a variety of information to healthcare workers. Information 109 is communicated to and transmitted from the information strip 100 via contacts 105.

Figure 4:
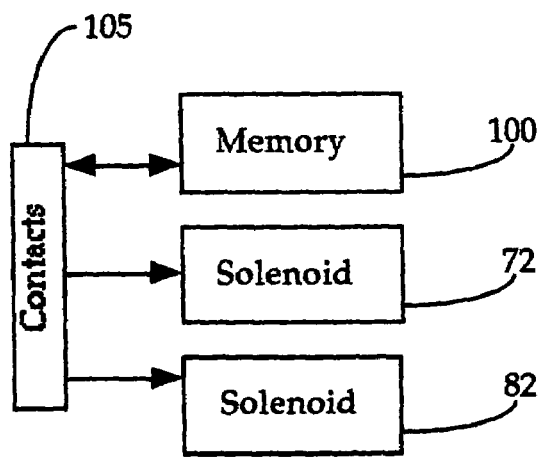
FIG. 4 is a schematic view of the circuitry of a cassette having a memory, shutter solenoid, locking solenoid and contacts that are controlled by an external computer processor.

The processor 90, battery 92 and display 94 can be omitted from the control portion 60 of the cassette 10 as shown in FIG. 4. In this embodiment, power is supplied to the solenoids 72 and 82 from the dispensing machine 150. As discussed below, the dispensing machine 150 includes a dispenser 160 that forms the electrical connections through which power is supplied via the contacts 105 to the solenoids 72 and 82, and display 94. As stated above, information 109 is communicated to and transmitted from the information strip 100 directly from the contacts 105.

The cassette contains a variety of information which is printed on a textural label 95 (see (FIG. 1)) or is stored in the information strip 100. (see (FIGS. 2 and 9)) The printed label 95 contains a variety of textual information, such as the type or name of the medication 5 in the cassette 10, the initial quantity of doses in the cassette, the manufacturer lot number, the expiration date of the medication, the date the hospital pharmacy or pharmaceutical manufacturer filled the cassette 10, and a serial number that identifies the particular cassette. The printed label 95 also includes a bar code containing some or all of this information. The printed label 95 is applied to the cassette 10 after medication is inserted into the cassette. The information strip 100 is preferably secured to the inside surface 66 of the control portion 60 so that it is not bumped and damaged during use. The information strip 100 can also be secured to the label 95 to obtain an electric label. The information strip 100 is in electrical communication with the processor 90, or if no processor is provided, with electrical contacts 105. These contacts 105 pass through the wall 62 of the control portion 60 and extend a small distance out from the outer surface 27 of the housing 15.

The information strip 100 contains a variety of information 109 as shown in FIG. 9. Prior to filling the cassette 10 with medication 5, the information strip 100 contains information 109a pertaining to the cassette 10 such as communication encryption codes, end of battery life information, and an identification number for identifying that particular cassette. As discussed below, most information 109b and c is communicated to the information strip via computerized pharmacy and hospital floor workstations 120 and 150, the information strip 109 is altered or updated to include all or some of the information on printed label 95.

Filling Cassette 10 with Medication 5 from Bulk Container 110

Figure 5:
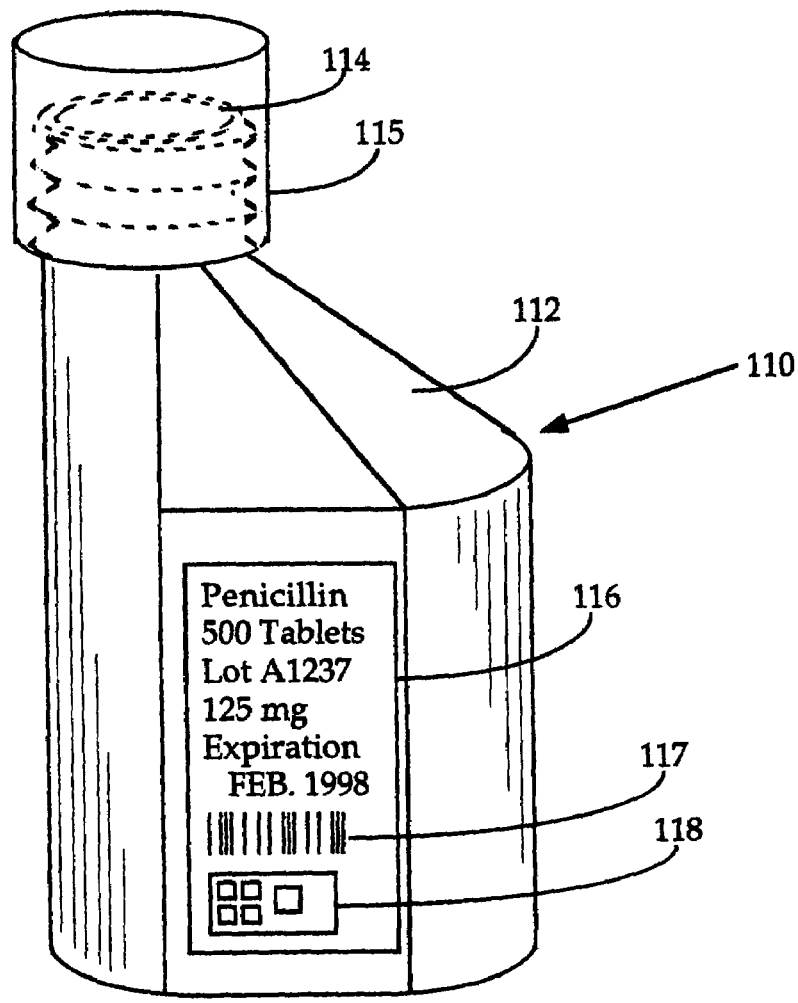
FIG. 5 is a perspective view of a bulk medication container having a label with written text, a bar code, and an electronic memory strip.

The hospital pharmacy contains a number of bulk medication containers 110 such as the one shown in FIG. 5. The bulk container 110 is typically supplied by a pharmaceutical manufacturer and includes a large quantity of a specific type of medication 5. The bulk container 110 has a body 112 with an open top 114 sealed by a cap 115. The type of medication 5 stored in the bulk container 110 is printed on a label 116 affixed to the outside surface of the bulk container. This printed label 116 contains information, such as the type or name of the medication 5, the initial quantity of doses in the container, the manufacturer lot number, and the expiration date of the medication. The printed label 116 also includes a bar code 117 containing some or all of this information. The label 116 is preferably an electronic label that includes a memory or information strip 118. As shown in FIG. 6, the electronic label or information strip 118 contains a variety of information 119 that includes all or some of the information on the printed label 116. As discussed below, the bar code 117 and electronic label 118 are used to electronically or optically transfer information 119 to the information strip 100 of the cassette 10.

Figure 7:
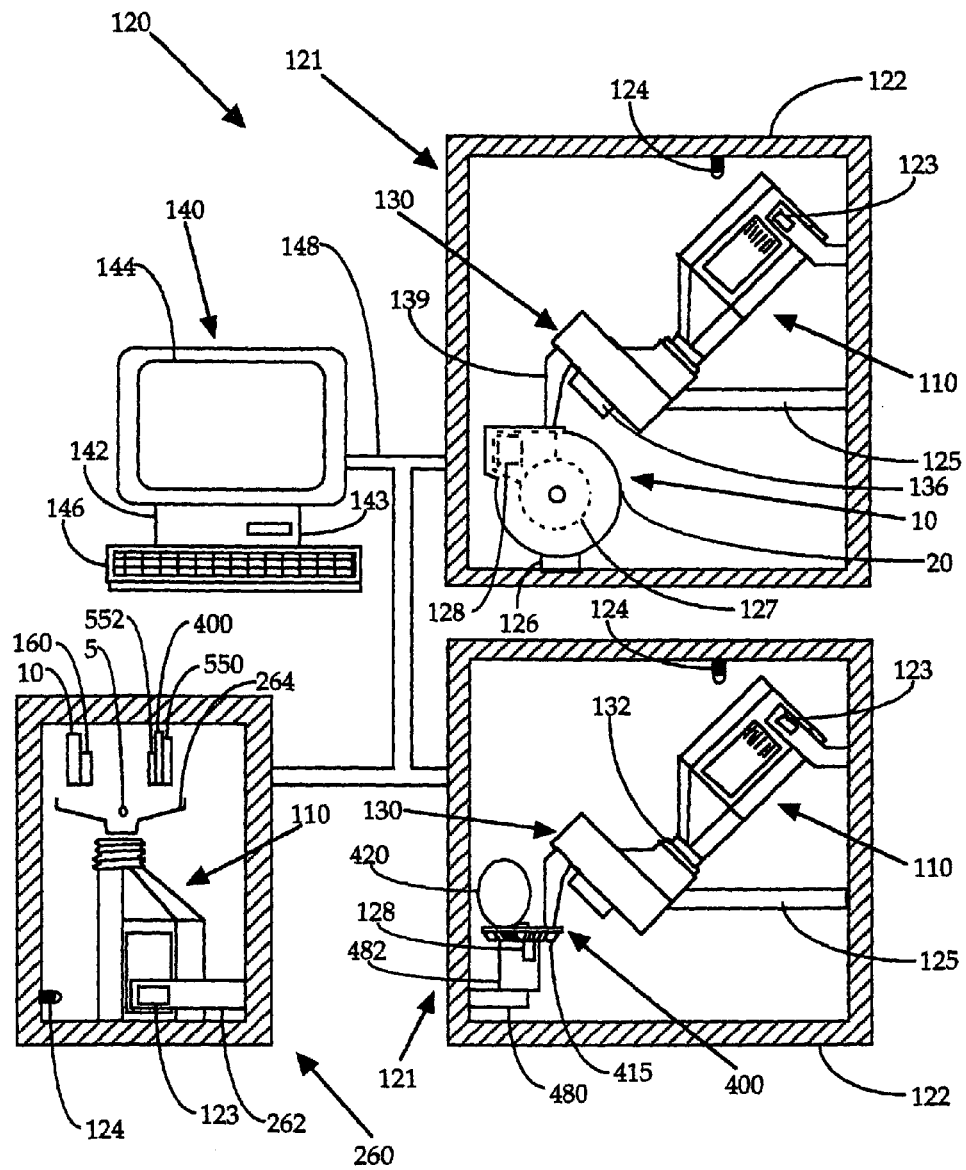
FIG. 7 is a plan view of a pharmacy work station including a computer control system for controlling the operation of a rotating wheel cassette filling machine, a blister pack cassette filling machine and a bulk container filling machine.

The pharmacy includes a workstation 120 for filling the cassettes 10. As shown in FIGS. 7 and 8, the pharmacy workstation 120 includes a dispensing machine 121, a singulator 130 and a computer control system 140. The dispensing machine 121 has a housing 122 that forms a compartment for holding the bulk container 110 and singulator 130. The dispensing machine 121 includes a mechanism 123 for reading and writing to the electronic label 118 of the bulk container 110, and a bar code reader 124 for reading the bar code 117 on the printed label 116. The dispensing machine 121 also includes a support 125 for holding the bulk container 110 and singulator 130 in an inverted position and joining them to the dispensing machine. The support 125 aligns the reading and writing mechanism 123 with the information strip 118 of the bulk container 110. The support 125 includes wires (not shown) or other means for supplying power to and communicating with the singulator 130.

The dispensing machine 121 also includes a cassette positioning mechanism 126 for holding one of the cassettes 10 with the openings 32 and 64 of the cassette facing up, and joining the cassette to the dispensing machine 121. The cassette positioning mechanism 126 includes a mechanism 128 for reading and writing to the information strip 100. The cassette positioning mechanism 126 also positions or aligns the information strip 100 with the reading and writing mechanism 128. The cassette positioning mechanism 126 is equipped with a drive key and motor (not shown) for engaging drive slot 35 and rotating wheel 40 of the cassette 10 during the filling process, as discussed below.

The dispensing machine 121 and singulator 130 are remotely controlled via the computer control system 140. The computer control system 140 includes a processor 142 having an associated memory device 143, a display or monitor 144, a keyboard 146 and a communication channel 148 to the dispensing machine 121. The healthcare worker uses the computer control system 140 to communicate with and operate the dispensing machine 121 and singulator 130 during the filling of the cassettes 10. While the computer control system 140 is shown as a separate computer system from the dispensing machine 121, it should be understood that the computer control system could be an integral part of the dispensing machine. It should be further understood that the memory device 143 associated with the processor 142 could be an integral part of the computer control system 140 or it could be a part of a hospital administration or pharmacy database network system.

The singulator 130 is removably connected to the support 125 of the dispensing machine 121. The singulator 130 is removed from the dispensing machine 121 and emptied of any medication 5 before it is secured to a predetermined bulk container 120 containing a specific type of medication 5. As best shown in FIG. 8, the singulator 130 has an opening 132 that is threadably secured to the open top 114 of the bulk container 110. The bulk container 110 and singulator 130 are inverted so that the medication 5 flows or drops into the singulator. The singulator 130 is then placed back in the dispensing machine 121 and secured to support 125. The singulator 130 operates in basically the same manner as a conventional, remotely controlled singulator. It separates a single, discrete dose of medication 5 from the other doses in the bulk container 110, and dispenses the single dose of medication through a discharge opening and into a funnel 139 secured to the discharge opening.

A completely or partially empty cassette 10 is placed in the dispensing machine 121 and secured to the cassette positioning mechanism 126. The bulk container 110 and singulator 130 are then inserted in the dispensing machine 121. The singulator 130 is secured to the support 125 so that it is in electrical communication with the computer control system 140 and power is being received by a motor 136 of the singulator. The funnel 139 is aligned with the cassette 10 to guide the dose of medication 5 through the openings 32 and 64 in the cassette.

Upon instruction from the computer control system 140, the motor 136 of the singulator 130 separates a single dose of medication 5 and advances the medication through its discharge opening, where the medication falls through the funnel 139 and openings 32 and 64 and into one of the cells 50 of the cassette 10. A sensor (not shown) can be provided to ensure that medication 5 is actually dispensed from the singulator 130 and into the cassette 10. The shutter 71 is in its open position 73 during this filling process. The computer control system 140 then instructs the reading and writing mechanism 123 to alter the information 119 in the electronic label 118 to indicate that the quantity of medication 5 in the bulk container 110 has been reduced. The computer control system 140 also instructs reading and writing mechanism 128 to alter the information 109 in the information strip 100 of the cassette 10 to add information 109b indicating that this predetermined dose of this type of medication 5 has been dispensed into this particular cassette. The information strip 100 can also be altered to include additional information 109b about this predetermined dose of medication 5.

A cassette positioning motor 127 then rotates wheel 40 through a specific degree of rotation to align openings 32 and 64 with another predetermined empty cell 50. Another predetermined dose of medication 5 is then dispensed into this other cell 50, and the information 109 and 119 in the information strip and electronic label 100 and 118, respectively, are altered to indicate that the bulk container 110 has been reduced and the other cell 50 has been increased by this predetermined dose of medication 5. This dispensing of medication 5 is repeated until the cassette 10 is filled with a desired quantity of the medication 5. Although the cells 50 are shown to contain a single dose of the same type of medication 5, it should be understood that different cells could contain different doses of medication or different types of medication, or both. For example, each cell 50 can be filled with a single or multiple dose of medication 5.

Once the cassette 10 is filled with a desired quantity and type of medication, the shutter 71 is moved into its closed position 74 by solenoid 72 and the locking pin 81 is moved into its locked position 83 by solenoid 82. The filled, closed and locked cassette 10 is now ready to leave the pharmacy for delivery to one of the hospital floor dispensing machines 151. In this manner, the medication 5 in the bulk container 110 is used to fill the cells 50 of the cassettes 10 while maintaining control over the access to the medication outside of the pharmacy.

As shown in FIG. 9, the information strip 100 of the cassette 10 now contains a variety of information 109a and 109b. The information strip 100 contains identification information that identifies the specific cassette 10 to which it is attached. The information strip 100 contains information about the quantity and type of medication 5 in each cell of the cassette 10. The information strip 100 contains information about the date each dose of medication 5 was dispensed in the cassette 10 and the pharmacy healthcare worker that dispensed the medication into the cassette. The information strip 100 may also contain information obtained from the electronic label 118, such as information identifying the pharmaceutical manufacturer of each dose of medication 5 in the cassette 10 and the expiration date of each dose. Other information can be stored in information strip 100 as well. For example, the pharmacy healthcare worker is also able to use the keyboard 146 to enter information that is stored in the information strip 100, such as any malfunction information pertaining to the past uses of the cassette 10 or special notes or warnings regarding the medication in the cassette.

Inserting Cassette 10 in Dispensing Machine 151

Figure 10:
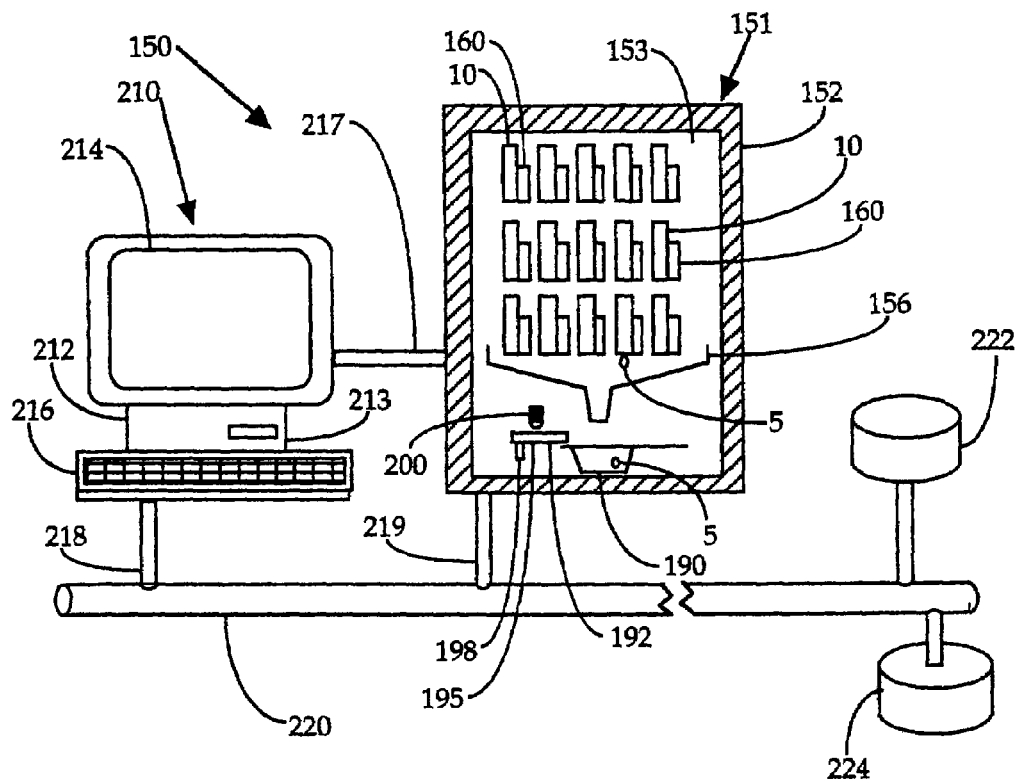
FIG. 10 is a plan view of a hospital floor workstation including a dispensing machine holding a plurality of dispensers and cassettes, and a computer control system in communication with the dispensing machine and hospital administration and pharmacy databases.

The filled and locked cassette 10 is transported to one of the hospital floor workstations 150 and dispensing machines 151 shown in FIG. 10. The dispensing machine 151 has a housing 152 that defines an interior compartment 153. The compartment 153 is designed to hold a number of dispensers 160 and cassettes 10. A tray or funnel 156 is located below the dispensers 160. The housing 152 has a door (not shown) for loading and removing the cassettes 10 from the dispensing machine 151. This door remains locked during use. Only authorized healthcare workers, such as the pharmacy staff, have access to open this door. Medication 5 dispensed from the dispensers 160 falls onto the tray 156 and is directed into a portable container 190, as discussed below.

Figure 11:
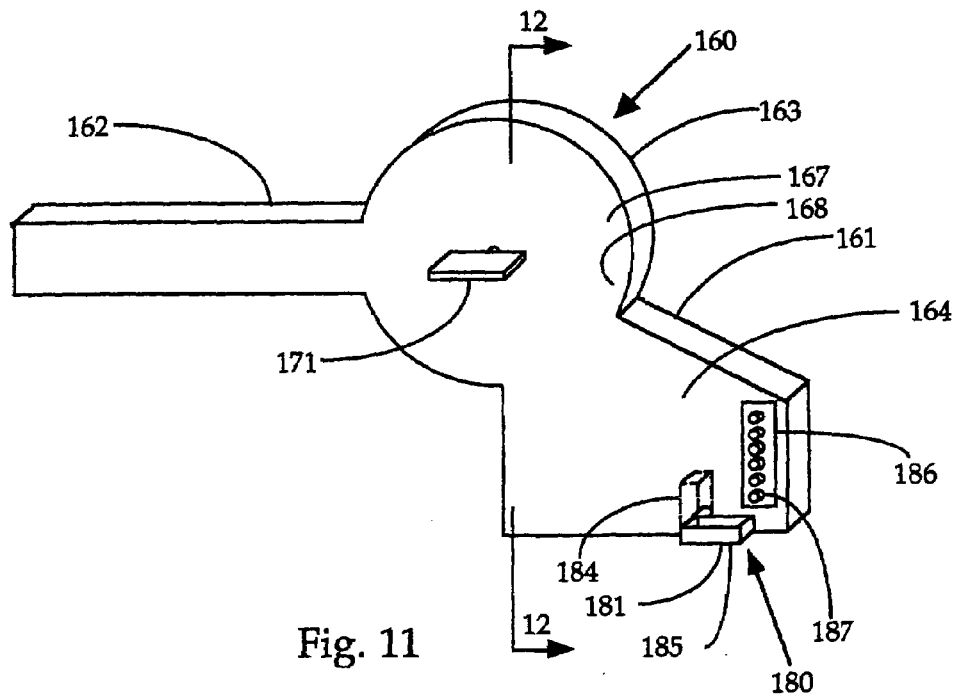
FIG. 11 is a perspective view of a dispenser showing its electrical contacts, drive key and locking pin.

The dispensers 160 are best shown in FIGS. 11–13. Each dispenser 160 has an integral housing 161 that includes a support arm 162, a disk shaped portion 163 and a control portion 164. The dispenser 160 is mounted in the dispensing machine 151 via support arm 162. The mounted end of the support arm 162 is provided with a variety of electrical connections (not shown) that are in electrical communication with a computer control system 210 of the workstation 150. The disk shaped portion 163 of the dispenser 160 has a central axis 165 and is smaller in diameter than the disk shaped portion 20 of the cassette 10. The control portion 164 extends radaily outward from the disk shaped portion 163. It has a box-shape that is aligned with and somewhat similar to the control portion 60 of the cassette 10. The three portions 162, 163 and 164 of the dispenser 160 share a common side wall 167. This side wall 167 has an outer surface 168 that is generally flat and shaped to smoothly engage the first side wall 22 of the cassette 10.

As discussed above, the dispenser 160 includes the drive mechanism 170 for rotating the inner wheel 40 of the cassette 10. The drive mechanism 170 includes a drive key 171 aligned parallel to the central axis 165 of the dispenser 160, and projects from the outer surface 168 of the side wall 167 of the dispenser. The drive key 171 is driven by a dispensing motor 172 located inside the disk shaped portion 163.

The dispenser 160 also includes a locking mechanism 180 for locking the cassette 10 to the dispenser. The locking mechanism 180 is located in the control portion 164 of the dispenser 160. The locking mechanism 180 includes an L-shaped locking bar 181 that projects from the outer surface 168 of side wall 167. The locking bar 181 is driven by a motor 182 located inside the control portion 164. The motor 182 selectively rotates the locking bar 181 between locked and unlocked positions 184 and 185, respectively, as shown in FIG. 11. The dispenser 160 also includes a sensing or reading and writing mechanism 186 having a number of electrical contacts 187 that project from the surface 168 of the dispenser housing 161. Power is supplied to solenoids 72 and 82 and information is transmitted to and from information 109 strip 100 via electrical contacts 187. These electrical contacts 187 are connected to the electrical contacts (not shown) going to the computer control system 210 of workstation 150.

The locking bar 181 and electrical contacts 187 are positioned at predetermined locations on the control portion 164 of the dispenser 160 so that they engage slot 36 and electrical contacts 105 of the cassette 10, respectively, as shown in FIG. 12. The cassette 10 is releasably connected to the dispenser 160 by aligning the central axis 25 of the cassette 10 with the central axis 165 of the dispenser, inserting the drive key 171 into the drive key slot 35, and rotating the locking bar from its unlocked position 185 to its locked position 184. The locking bar 181 is rotated by motor 182 to secure the cassette 10 to the dispenser 160.

The information strip 100 is now in electrical communication with the computer control system 210 of the workstation 150. The control system 210 includes a computer processor 212 with an internal clock, memory device 213, monitor 214, and keyboard 216. The computer processor 212 gathers the medication information 109 from each cassette 10 in the machine 151 via communication cable 217. The inventory information includes information such as a total actual quantity of each type of medication in the dispensing machine 151, the date the medication was dispensed into its particular cassette, and the batch number and expiration date of the medication in each cassette in the machine and for the machine as a whole. This inventory information is obtained by a healthcare worker via the monitor 214 and keyboard 216. An alarm (not shown) sounds if the quantity of a given type of medication 5 falls below a predetermined level or if the expiration date of a particular medication is reached or surpassed. The computer processor 212 communicates this inventory information and other information 109 to its associated memory device 213.

Communication cables 218 and 219 connect the computer control system 210 and the dispensing machine 151 to a hospital network 220, respectively. The hospital network 220 includes an administration database 222 and a pharmacy database 224. By linking the dispensing machines 151 to databases 222 or 224, the medication distribution and inventory system obtains total or comprehensive inventory information for all or most of the medication in the hospital and pharmacy medication system, as shown in FIG. 17. Similar to the memory device 143 for the pharmacy computer control system 140, it should be understood that the associated memory device 213 for the computer control system 210 can be an integral part of the computer control system 210 or a remote memory device such as in the hospital administration or pharmacy database systems via the hospital network 220.

Dispensing Medication 5 from Cassette to Portable Container 190

Healthcare workers use the workstation 150 to control the operation of the dispensing machine 151. As noted above, workstation 150 is in communication with databases 222 and 224, which contain a variety of information 229, such as that shown in FIG. 17. Physicians enter patient prescription information into the hospital or pharmacy databases 222 or 224. By simply entering a patient name or other patient identifying information, a healthcare worker can instruct the dispensing machine 151 to dispense a specific quantity of medication 5 prescribed by a physician for that particular patient. This is done by identifying the cassette 10 and information strip 100 having appropriate medication type and quantity information 109*b*, and instructing the dispensing machine 151 to dispense the specific quantity of the appropriate medication 5 from that cassette. Information and instructions sent to or from the workstation 150 and the dispensing machine 151 are also sent via the network 220 to the hospital administration and pharmacy data bases 222 and 224.

Wheel drive motor 172 is activated to rotate the drive key 171 and inner wheel 40 a predetermined radial degree of rotation. This incremental rotation of the wheel 40 aligns one of the various cells 50 of the cassette 10 with medication dispensing openings 32 and 64. The specified quantity of medication 5 is then dispensed when shutter 71 is moved into its open position 73 by solenoid 72 as best shown in FIG. 13. The computer processor 212 alters the information 109*b* in information strip 100 to indicate that the quantity of medication 5 in the cassette 10 was reduced by the specified quantity. The computer processor 212 also obtains dispensing date and time information from its internal clock, predetermined patient information, prescribing physician information and healthcare worker information and transmits this information 109*c* for writing to the information strip 100 via sensing mechanism 186. The computer processor 212 also updates the inventory information in its associated memory device 213 to indicate this reduction in the quantity of medication in this particular cassette 10. That is, the computer processor 212 updates the inventory information of the associated memory device 213 to indicate that the total actual quantity of that particular type of medication in the machine 151 was reduced by an amount equal to the specified quantity of medication just dispensed. The processor 212 transmits this and other updated or additional information 109*b* and 109*c* to its databases 222 and 224.

Medication 5 dispensed from the cassettes 10 in the dispensing machine 151 falls onto tray 156 which directs the medication into portable container 190. A sensor (not shown) can be provided to ensure that the medication 5 is actually dispensed from a cassette 10. The portable container 190 is then sealed with a lid 192 containing an information device 195. The lid 192 includes a locking device 198 that locks the portable container 190 closed until the portable container is brought to a specific patient in one of the hospital rooms. The information device 195 initially contains some information 199*a*, such as an identification number, encryption codes, battery life information, and past history information relating to the past use and repairs to the lid. The dispensing machine 151 and computer control system 210 transmit a variety of patient and medication information 199*b* to the information device 195 via a mechanism 200 for reading and writing to the information device 195 as shown in FIG. 14. This dispensing information 199*b* includes, among other things, medication information identifying the type and quantity of medication dispensed to the portable container 190, patient information identifying the person that was prescribed this medication, physician information identifying the name of the prescribing physician, dispensing information identifying the time the medication was dispensed into the portable container 190, the healthcare worker that dispensed the medication, and healthcare worker authorization information specifying the level of worker that is authorized to administer this medication.

The healthcare worker then transports the portable container 190 to the desired patient 240 as shown in FIG. 15. The patient 240 is wearing a wristband 242 containing specific patient information 249 as shown in FIG. 16. The information 249 in the patient's 240 wrist band 242 is compared to the predetermined patient information 199 in the information device 195 to verify that the prescribed medication is being given to the correct patient 240. A healthcare worker badge (not shown) containing healthcare worker information can also be compared to the healthcare worker information in the information device 195 to ensure that the healthcare worker is authorized to administer this medication 5. Upon opening the portable container 190, the information device 195 will presume all the medication 5 was given or administered to and consumed by the patient 240. If only a portion of the medication 5 is given to the patient 240, the healthcare worker can update the information device 195 to reflect the amount of medication given and the amount of medication left in the portable container 190. This consumption information 199c pertaining to the administration of the medication to the patient is stored in the information device 195.

The portable container 190 is then returned to the workstation 150, dispensing machine 151 or some other location such as the hospital pharmacy. The dispensing and consumption information 199b and 199c in the information device 195 is then downloaded to the information 229 in the hospital network 222 and 224, thereby contributing to the information 229 shown in FIG. 17. Any medication remaining in the portable container 190 is returned to the dispensing machine 151 for pick up by the pharmacy staff, or the unused medication can be returned directly to the hospital pharmacy. This unused medication 5 can then be returned to the appropriate bulk container 110 in a manner similar to that discussed below.

Returning Medication 5 in Cassette 10 to Bulk Container 110

As shown in FIG. 7, unused medication 5 remaining in the cassettes 10 is returned to the appropriate bulk containers 110 in the hospital pharmacy via dispensing machine 260 of the pharmacy dispensing workstation 120. First, the hospital floor dispensing machine 151 is unlocked and the desired cassette 10 containing unused medication 5 is removed. This cassette 10 is then returned to the pharmacy and placed on a dispenser that is the same as or similar to the dispensers 160 of the dispensing machine 151. The appropriate bulk container 110 is placed in the dispensing machine 260 and joined to support arm 262 so that its reading and writing mechanism 123 is aligned in communication with electronic label 118.

The pharmacy computer control system 140 then reads the medication type and quantity information 109b on the information strip 100. The control system 140 also reads the information 119 on the information strip 118 of the bulk container 110 to ensure that the correct bulk container 110 is matched with the type of unused medication 5 in the cassette 10. An alarm (not shown) sounds if the medication type information of the bulk container 110 does not match the medication type information of the cassette 10. The control system 140 then activates the motor of the dispenser 160 to rotate the cassette 10 a complete rotation. The medication 5 in the cassette 10 falls onto tray 264 and into the bulk container 110. The control system 140 then uses the quantity information 109 in the cassette 10 to alter the information strip 118 of the bulk container 110 to reflect that it has had a given quantity of medication added to the bulk container. The control system 140 also alters the quantity information 109b in the information strip 100 of the cassette 10 to indicate that it has had this same quantity of medication removed. This is done until all the medication 5 in the cassette 10 has been returned to the bulk container 110.

Cartridge Cassette 300

In a second embodiment of the invention, the cassette takes the form of a cartridge 300 filled with a number of unit dose blister packs 350 as shown in FIGS. 18–20. The cartridge shaped cassette 300 has a rectangular shaped housing 301 having inside and outside surfaces 302 and 303. The cartridge 300 is formed by two side walls 304, top and bottom walls 305 and 306, and a rear wall 307 that closes one end of the cartridge. The other end 308 of the cartridge 300 is open for inserting and removing medication 5. The inside surface 302 of the cartridge forms an interior or compartment 310.

The cartridge 300 includes a hanger 315 in compartment 310 for holding the blister packs 350. One end 316 of the hanger 315 is secured to the inside surface 309 of the rear wall 307 proximal the top wall 305. The hanger 315 is cantilevered from its point of securement and spans the length of the cartridge to just inside the open end 308. The hanger 315 has a free end 317 that is bent upwardly to help prevent blister packs from inadvertently sliding off the hanger. A door or access panel 320 is secured to the open end 308 of the top wall 305 via a living hinge 322. The door 320 is movable from open and closed positions 323 and 324. Medication 5 can be inserted or removed from the cartridge 300 when the door is in its open position 323. The door 320 closes the open end 308 when in a closed position 324 to prevent access to the medication 5 inside the cartridge 300. A seal 325 is placed over the door 320 to help prevent unauthorized access to the medication 5 during transport to and placement in dispensing machine 151.

The cartridge 300 includes a printed label 326 secured to the outside surface 303 of the housing 301. Similar to the printed label on the cassette 10, this printed label 326 contains a variety of information, such as the name of the medication 5 in the cartridge 300, the initial quantity of doses in the cartridge, the manufacturer lot number of the medication, and the expiration date of the medication. The printed label 326 also includes a machine readable bar code 327 containing some or all of this information.

An information strip 340 is secured to the outside surface 303 of the cartridge 300. The information strip 340 is functionally and structurally similar to information strip 100 of cassette 10. It also contains information 109 similar to that in the information strip 100. The information strip 340 can be a part of label 326 to produce an electronic label.

The unit dose blister packs 350 serve as partitions for separating the medication 5 into single doses. The blister packs 350 have a basically standard commercially available construction containing a tear resistant sheet 352 and a backing sheet 354. The tear resistant sheet 352 and backing sheet 354 combine to form a pocket that holds the medication 5. Each unit dose blister pack 350 contains a single dose of medication 5. These packets 350 can be supplied directly by a pharmaceutical manufacturer. Each packet contains an aperture 355 for engaging hanger 315. Each packet 350 also contains a printed label 356 and a bar code label 358 containing information about the medication and the pharmaceutical manufacturer.

These cartridges 300 and blister packs 350 are particularly suited for use in conjunction with a dispensing machine (not shown) that houses a number of filled cartridges. The dispensing machine utilizes a movable, computer controlled arm that grabs the unit dose blister packs 350 via vacuum suction, removes them from their cartridge and dispenses them from the machine. A dispensing machine of this type is currently being manufactured by Automated Healthcare, Inc. of Pittsburgh, Pa. and Automated Prescription Systems, Inc. of Pineville, La., and is more fully described in U.S. Pat. Nos. 5,468,110 and 5,593,269. Each cartridge 300 contains one of a variety of types of medication 5. The dispensing machine interacts with the information strips 340 to keep track of the quantity of each type of medication 5 in the dispensing machine 151, and update the quantity information 109 in the information strips 340. The information strip 340 of each cartridge 300 contains information 109 regarding the actual type and quantity of medication remaining in the cartridge. This information 109 remains with the cartridge 300 when the cartridge is removed from one dispensing machine 151 and inserted into another or returned to the hospital pharmacy.

Blister Pack Cassette 400

FIGS. 21–28 show a third embodiment of the invention where the cassette is in the form of a multi-dose, disk shaped, blister pack 400 with an interactive label 450 having an information strip 460. The blister pack 400 is intended for use in a dispensing machine similar to that of dispensing machine 151. Information strip 460 is functionally and structurally similar to information strips 100 and 340. The operation of and interaction between the workstation 150, dispensing machine 151 and computer control system 210 is generally the same as for cassettes 10 and 300.

The blister pack 400 is formed by a tear resistant sheet 411 having front and rear surfaces 412 and 413 and a perimeter 414. The tear resistant sheet 411 is formed into multiple pockets 415 located around its perimeter 414. Each pocket or cell 415 holds a single dose of medication 5. The tear resistant sheet 411 has a substantially flat central area 416 with a central opening 417 and offset notch 418 formed through the sheet 411. The rear surface 413 of the tear resistant sheet 411 has an adhesive coating 419 applied to it, except in pockets 415. The blister pack also includes a backing sheet 420 having front and rear surfaces 422 and 424. The front surface 422 of the backing sheet 420 is secured to the rear surface 413 of the tear resistant sheet 411 via the adhesive coating 419. The backing sheet 420 extends over the pockets 415 so that each dose of medication 5 is sealed into its respective pocket. The tear resistant sheet 411 has perforations 430 that separate each pocket 415 into a discrete portion 432 that is separable from the remainder of the container. In this third embodiment, the pockets 415 form a multi-compartment interior of the blister pack cassette 400. Similar to the second embodiment, the discrete portions 432 form the partitions that separate the discrete doses of medication 5.

An interactive label 450 is attached to the flat, central area 416 of the front surface 412 of the tear resistant sheet 411 via an adhesive layer 451. The label 450 has a textual portion 452 with prescription information printed on its front surface. The information in the information strip 460 is the same as the information 109 in the first and second embodiments. The electronic information strip 460 is sensed through its contacts 462 via an electrical connection or wire 464.

Filling Blister Pack Cassette 400 with Medication 5 from Bulk Container 110

Similar to the filling of rotating wheel cassette 10 above, the blister pack cassette 400 is filled in a hospital pharmacy from the bulk medication containers 110. (See FIGS. 5–7.) As stated above, the pharmacy includes a workstation 120 for filling the blister pack cassettes 400. The cassette filling workstation 120 includes a dispensing machine and singulator that are the same as or similar to the dispensing machine 121 and singulator 130 used to fill the rotating wheel cassette 10. The dispensing machine 121 and singulator 130 for the blister pack cassette 400 are controlled by the computer control system 140. The dispensing machine 121 has a housing 122 that forms a compartment for holding the bulk container 110 and singulator 130. The dispensing machine 121 includes a mechanism 123 for reading and writing to the electronic label 118 of the bulk container 110, and a bar code reader 124 for reading the bar code 117 on the printed label 116. The dispensing machine 121 also includes a support 125 for holding the bulk container 110 and singulator 130 in an inverted position. The support 125 aligns the reading and writing mechanism 123 with the electric label 118 of the bulk container 110. The support 125 includes wires (not shown) or other means for supplying power to and communicating with the singulator 130.

The dispensing machine 121 includes a cassette positioning mechanism 480 for holding and aligning one of the blister pack cassettes 400 in a predetermined position with the open end of the pockets 415 facing up. The blister pack cassette positioning mechanism 480 includes a reading and writing mechanism that is the same as or similar to that reading and writing mechanism 128 for the rotating wheel cassette 10. The cassette positioning mechanism 480 is equipped with a drive key (not shown) for engaging central opening 417 and offset notch 418 of blister pack cassette 400 during the filling process.

The dispensing machine 121 and singulator 130 are remotely controlled via the computer control system 140. The healthcare worker uses the computer control system 140 to communicate with and operate the dispensing machine 121 and singulator 130 during the filling of the cassettes 400. Again, while the computer control system 140 is shown as a separate computer system from the dispensing machine 121, it should be understood that the computer control system could be an integral part of the dispensing machine.

A completely or partially empty cassette 400 is placed in the dispensing machine 121 and secured to the cassette positioning mechanism 480. The backing sheet 420 has not been secured yet, so that the pockets 415 are still exposed. The bulk container 110 and singulator 130 are fastened together and inserted in the dispensing machine 121. The singulator 130 is secured to the support 125 so that it is in electrical communication with the computer control system 140 and power is being received by the singulator motor 136. The funnel 139 is aligned with the blister pack cassette 400 to guide the dose of medication 5 into an empty pocket 415 of the cassette.

Upon instruction from the healthcare worker using the computer control system 140, the motor 136 of the singulator 130 separates a single dose of medication 5 and advances the medication through its discharge opening, where the medication falls through the funnel 139 and into one of the pockets 415 of the cassette 400. The computer control system 140 then instructs the reading and writing mechanism 123 to alter the information 119 in the electronic label 118 to indicate that the quantity of medication 5 in the bulk container 110 has been reduced. The computer control system 140 also instructs the reading and writing mechanism 128 to alter the information 109 in the information strip 460 of the cassette 400 to indicate that this predetermined dose of this type of medication 5 has been dispensed into this particular pocket 415 of the cassette. The information strip 460 can be further altered to include additional information 109 about this predetermined dose of medication 5.

A cassette positioning motor 482 then rotates the disk shaped blister pack 400 through a specific degree of rotation to align the funnel 139 with another empty pocket 415. Another predetermined dose of medication 5 is then dispensed into this other pocket 415, and the information 109 and 119 in the information strip 460 and electronic label 118, respectively, are altered to indicate that the bulk container 110 has been reduced and the other pocket has been increased by this predetermined dose of medication 5. This dispensing of medication 5 is repeated until the cassette 400 is filled with a desired quantity of the medication 5. As with the cells 50 of the rotating wheel cassette 10 above, it should be understood that different pockets 415 could contain different doses of medication or different types of medication, or both. Once the blister pack cassette 400 is filled with a desired quantity and type of medication, the backing sheet 420 is applied over the pockets 415 to seal the medication into the cassette. The backing sheet 420 has to be broken or one of the discrete portions 432 of the blister cassette have to be removed in order to obtain medication 5 from the pockets 415 of the sealed blister pack cassette 400. This type of tampering can be easily detected by the hospital pharmacy personnel. The blister pack 400 can also be placed in a housing (not shown) during transit and operation to seal the blister pack in a manner similar to the housing 15 of the cassette 10. The filled and sealed cassette 400 is now ready to leave the pharmacy for delivery to one of the hospital medication dispensing machines 151. In this manner, the medication 5 in the bulk container 110 is used to fill the pockets 415 of the cassettes 400 while maintaining a measure of control over the access to the medication outside of the pharmacy.

As shown in FIG. 9, the information strip 460 of the blister pack cassette 400 is altered to include a variety of information 109. The information strip 460 contains identification information 109 that identifies the specific cassette 400 to which it is attached. The information strip 460 contains information about the quantity and type of medication 5 in each pocket 415 of the cassette 400. The information strip 100 contains information 1099 about the date each dose of medication 5 was dispensed in the cassette 400 and the pharmacy healthcare worker that dispensed the medication into the cassette. The information strip 460 may also contain information obtained from the electronic label 118, such as information identifying the pharmaceutical manufacturer of each dose of medication 5 in the cassette 400 and the expiration date of each dose. Other information can be stored in information strip 460 as well. For example, the pharmacy healthcare worker is also able to use the keyboard 146 to enter information that is stored in the information strip 460, such as any malfunction information pertaining to the past uses of the cassette 400 or special notes or warnings regarding the information in the cassette.

Dispensing Medication 5 from Blister Pack 400

Figure 25:
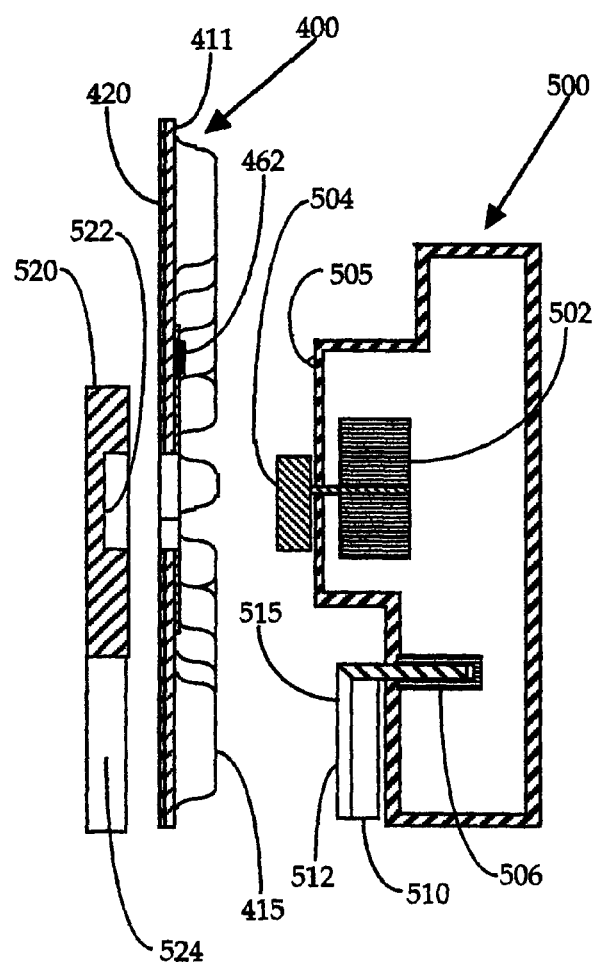
FIG. 25 is a cross-sectional, side plan view of a blister pack cassette having a drive slot and a locking slot aligned with a dispenser having a drive motor and a locking pin.
Figure 26:
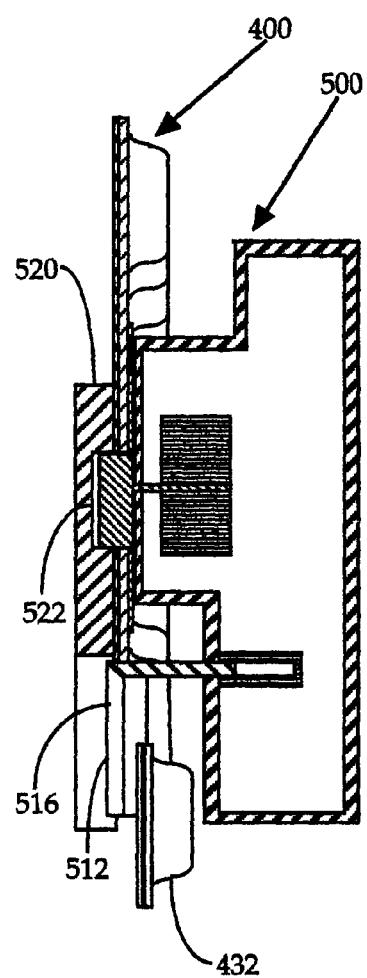
FIG. 26 is a cross-sectional, side plan view of a blister pack cassette secured to the dispenser.
Figure 27:
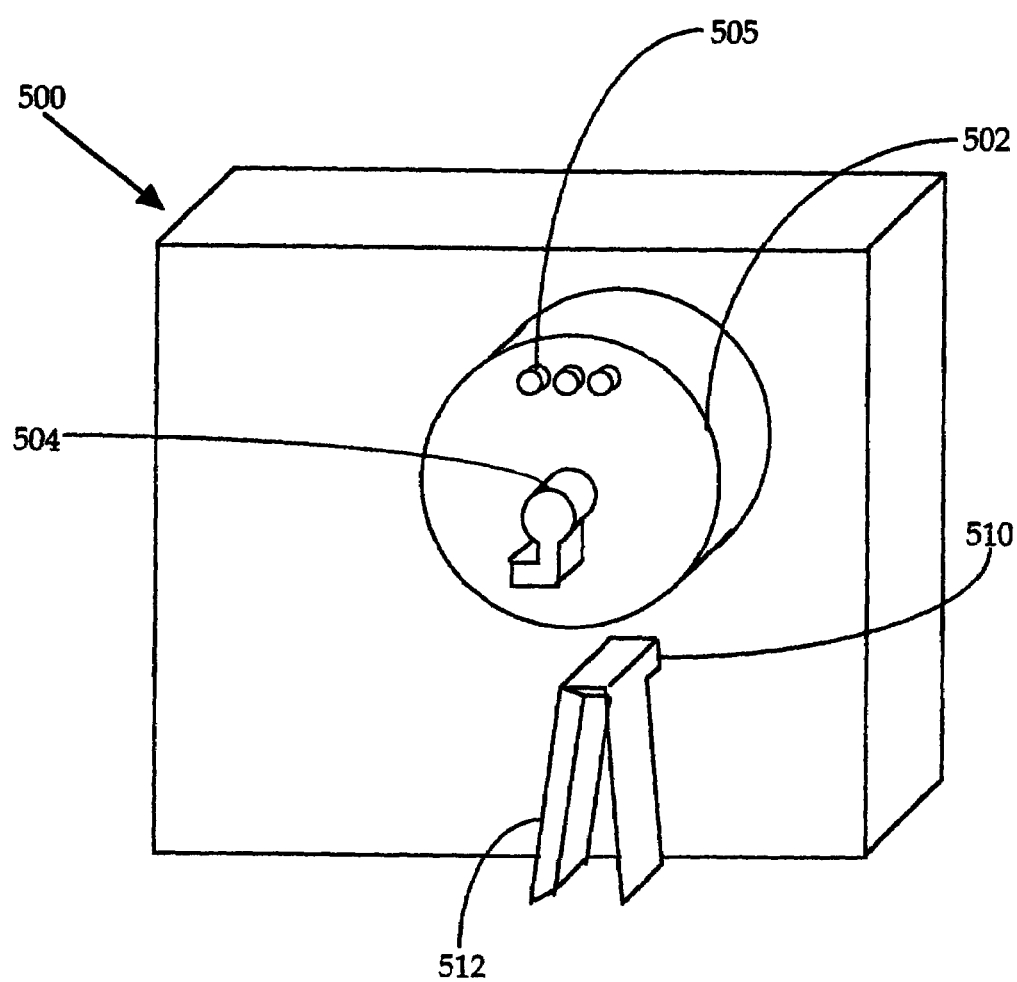
FIG. 27 is a perspective view of a dispenser for the blister pack cassette having a drive motor, drive key, contacts and a cutter.
Figure 28:
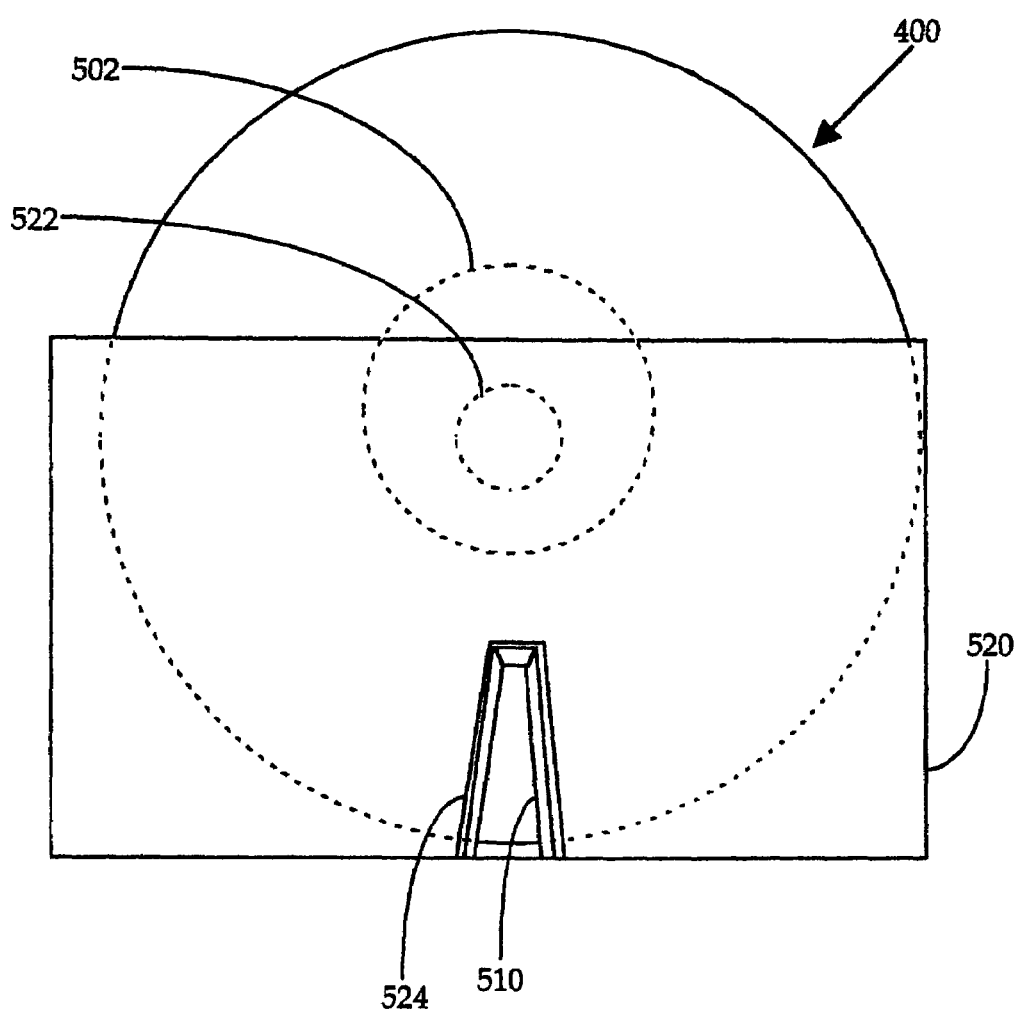
FIG. 28 is a rear, plan view of a dispenser holding a blister pack cassette.

As shown in FIGS. 25–27, the opening 417 and notch 418 in blister pack 400 are used to mount the multi-dose blister pack 400 into a predetermined position with a dispenser 500. The opening 417 and notch 418 ensure that the blister pack 400 is placed in a secure position with said dispenser 500, and that the sensing contacts 462 are aligned with contacts 505 for electrically communicating the information strip 460 with the computer control system 210. The dispenser 500 includes a dispensing motor 502 that rotates a drive key 504. The drive key 504 is shaped to matingly engage the central opening 417 and offset notch 418 of the blister pack 400. The shape of the drive key 504 and offset notch 418 align the contacts 462 of the blister pack with the contacts 505 of the dispenser 500. The rotation of the drive key 504 cause the contacts 462 to move out of alignment with contacts 505. Information pertaining to the dispensing of medication 5 from the cassette 400 is stored in the memory of computer processor 212. Before cassette 400 can be removed from dispenser 500, the cassette 400 must be rotated back to the position in which the cassette and dispenser contacts 462 and 505 are in alignment. When in this position, information stored in the memory of processor 212 is communicated via contacts 462 and 505 to interactive label 450.

Figure 24:
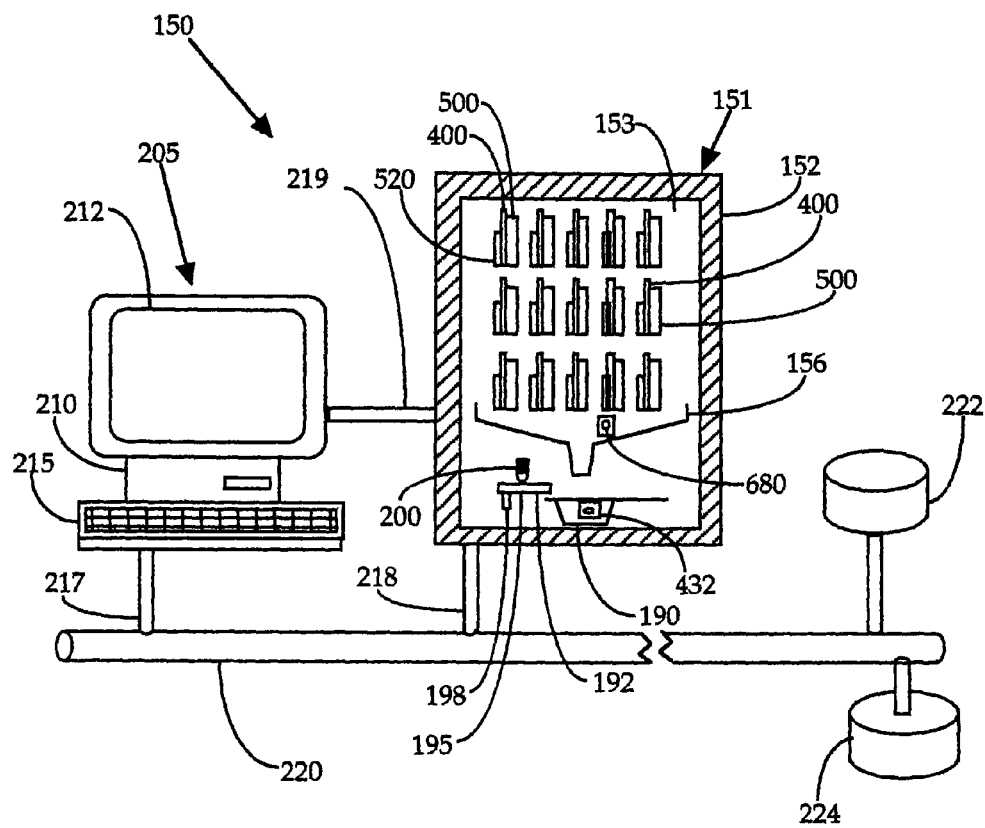
FIG. 24 is a plan view of a hospital floor workstation including a dispensing machine holding a plurality of dispensers and blister pack cassettes, and a computer control system in communication with the dispensing machine and hospital administration and pharmacy databases.

Rotation of the drive key 504 rotates the blister pack 400 so that one of the discrete portions 432 containing an individual dose of medication 5 is aligned over a cutter 510 having a V-shaped cutting edge 512. The V-shaped cutting edge 512 is shaped to engage the perforated edges 430 of the discrete portions 432 of the blister pack. A cutter solenoid 506 then causes the cutter 510 to move from its retracted position 515 to extend so that the cutter edge 512 engages and passes through the perforations 430 of the discrete portion 432. This cuts the discrete portion 432 from the remainder of the blister pack 400, so that it falls into tray 156 and into portable container 190 as shown in FIG. 24.

As shown in FIGS. 25 and 26, a support or backing plate 520 is provided to hold the blister pack 400 against the dispenser 500 and to provide a rigid surface for cutting the discrete portions 432 from the blister pack. The backing plate 522 includes a notch 522 for receiving the drive key 503, and a V-shaped slot 524 for receiving the cutter edge 512 when in its extended cutting position 516. The single dose of medication 5 still sealed inside the discrete portion 432 falls onto the tray 156 of the dispensing machine 151 and into the portable container 190 for delivery to the appropriate patient. Information 109 and 199 pertaining to the dispensing of the medication 5 is transmitted to the memory strip 460 of the blister pack cassette 400 and the information device 195 of the portable container 190, respectively. After the portable container 190 is transported to the patient, the discrete portion 432 is removed from the portable container 190 and the medication 5 is removed from the discrete portion for consumption by the patient. As state above, this consumption information 199c is stored in the information device 195.

Returning Medication 5 in Cassette 400 to Bulk Container 110

As shown in FIG. 7, unused medication 5 remaining in the blister pack cassettes 400 is returned to the appropriate bulk containers 110 in the hospital pharmacy via a dispensing machine 260 of the pharmacy dispensing workstation 120. This process is similar to the process of returning medication from the rotating wheel cassette 10 to the bulk container 110 as discussed above. First, the hospital floor dispensing machine 151 is unlocked and the desired cassette 400 containing unused medication 5 is removed. This blister pack cassette 400 is then returned to the pharmacy and placed on a dispenser 550 similar to the dispensers 500 of dispensing machine 151. The appropriate bulk container 110 is placed in the dispensing machine 260 and secured to support arm 262 so that its reading and writing mechanism 123 is aligned in communication with electronic label 118. The dispenser 550 includes a backing or support plate 552 similar to backing plate 520. The dispenser 550 and backing plate 552 are able to dislodge and separate the medication 5 from the discrete portion 432 of the blister pack. Only the medication 5 is dispensed back into the bulk container 110.

The pharmacy computer control system 140 then reads the medication type and quantity information 109 on the information strip 460. The control system 140 also reads the information 119 on the electronic label 118 of the bulk container 110 to ensure that the correct bulk container 110 is matched with the type of unused medication 5 in the cassette 400. An alarm (not shown) sounds if the medication type information of the bulk container 110 does not match the medication type information of the cassette 400. The control system 140 then activates the motor of the dispenser 260 to rotate the blister pack cassette 400 a complete rotation. The remaining medication 5 in the cassette 400 falls onto tray 264 and into the bulk container 110. The control system 140 then uses the quantity information 109 in the cassette 400 to alter the electric label 118 of the bulk container 110 to reflect that this dispensed quantity of medication has been added to the bulk container. The control system 140 also alters the quantity information 109 in the cassette 400 to indicate that this dispensed quantity of medication has been removed from the cassette 400.

Operation of Cassettes 10, 300 and 400

Figure 29:
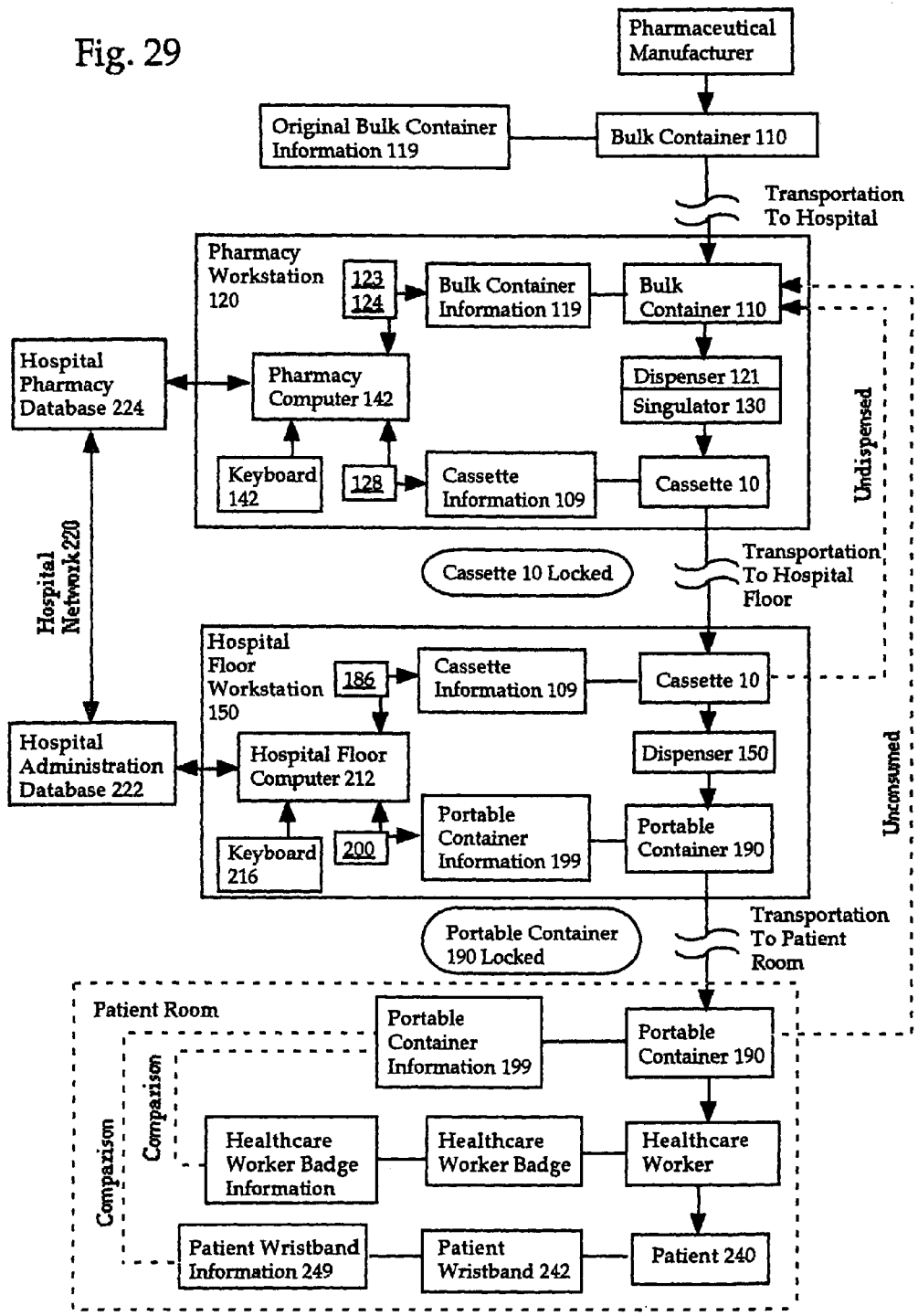
FIG. 29 is a flow chart showing a process of distributing medication and transferring information from a pharmaceutical manufacturer supplied bulk container to a hospital pharmacy, from the hospital pharmacy to a cassette that is inserted in a hospital floor dispensing machine, and from the cassette and hospital floor dispensing machine to a portable container that is taken to a patient room for administering the medication to a patient.

Although the operation of cassettes 10, 300 and 400 should be readily understood from the above, the following is provided to assist the reader. While this discussion is directed towards the rotating wheel cassette 10, it should be understood that this discussion is generally applicable to cartridge cassette 300 and blister pack cassette 400 as well. FIG. 29 provides a flow chart showing the process of distributing medication from a pharmaceutical manufacturer to the hospital pharmacy, from the hospital pharmacy to cassette 10, 300, or 400 which is transported to and inserted in a hospital floor dispensing machine 151. From the hospital floor dispensing machine, the medication 5 is dispensed to portable container 190 which is transported to a patient 240 for consumption by the patient. Undispensed medication 5 remaining in the cassette 10, 300, or 400 and unconsumed medication remaining in the portable containers 190 is returned to its appropriate bulk container 110 in the hospital pharmacy. During this process, information 109, 119 and 199 is transferred to and from workstations 120 and 150 and databases 222 and 224 via the cassette information strip 100, 340 or 460, bulk container electric label 118, portable container information device 195, as well as a variety of other components such as patient wrist band 242.

Pharmaceutical manufacturers supply bulk containers 110 with textual labels 116 that have bar code 117. The printed label 116 can be converted to an electric label by adding memory strip 118. The pharmaceutical manufacturer enters the information 119 into the bar code 117 and electric label 118. When the bulk container 110 arrives at the hospital pharmacy, some or all of the information 119 is transferred via the pharmacy workstation 120 to the pharmacy computer processor 142 and pharmacy database 224.

When a specific type of medication 5 is needed at hospital workstation 150, the bulk container containing that type of medication is connected to singulator 130 and placed in the pharmacy dispensing machine 121. A partially or completely empty cassette 10 is also loaded into the pharmacy dispensing machine 121. During the process of filling the cassette 10, the information strip 100 of the cassette 10 is altered via reading and writing mechanism 128 to transfer some or all of the information 119 on the bar coded label 116 or electric label 118 to the information strip 100. The information strip 100 is also altered to contain information accessible by processor 142, such as filling time information obtained from the internal clock of the processor, or other information entered from the keyboard 146. The pharmacy workstation 120 also alters the information 119 in the electronic label 118 of the bulk container 110 via the reading and writing mechanism 123 to contain information 119b such as the date, time and quantity of medication dispensed from the container 110 and the name of the person dispensing the medication.

After filling the cassette 10, the openings 32 and 64 of the cassette 10 are closed by shutter 71 and locked into this closed position 74 via shutter solenoid 72 to prevent unauthorized access to the medication 5 in the cassette 10. The cassette 10 is now ready for transportation to the appropriate hospital floor workstation 150. Workstation 150 activates solenoids 72 and 82 and unlocks the cassette 10. This is done after the cassette 10 is secured to dispenser 160 and installed in the dispensing machine 151, and the door to the dispensing machine 151 is locked shut.

The information 109 in the cassette 10 is transferred via hospital floor workstation 150 and reading and writing mechanism 186 to the dispensing machine 151 and computer processor 212. The hospital floor computer 212 compiles local inventory information gathered from each of the cassettes 10 in the dispensing machine 151. The hospital floor computer processor 212 transmits this local inventory information to the administration and pharmacy databases 222 and 224 via the hospital network 220. The pharmacy staff uses this local inventory information to determine if a particular type of medication should be delivered to a particular hospital workstation 150 and dispensing machine 151, or if any cassettes 10 at that workstation are empty and need to be returned to the pharmacy. The administration and pharmacy databases 222 and 224 are used to compile a total or comprehensive hospital inventory information. The pharmacy staff can use this comprehensive inventory information to determine which medications should be ordered from the pharmaceutical manufacturer.

Healthcare workers use workstation 150 to determine what medications 5 need to be dispensed and given to their patients 240. By entering the name or some other identification number for one of their patients 240, the computer processor 212 can determine from the administration or pharmacy databases 222 or 224 what medications have been prescribed by the physician(s) for the patient. The healthcare worker must also identify himself or herself in order to log on to workstation 150 or to dispense medication from dispensing machine 151.

When a predetermined dose of a specific type and quantity of medication 5 is dispensed from one of the cassettes 10 in a given dispensing machine 151, the associated computer processor 212 notes this occurrence by updating the local inventory information to indicate a reduction in this type and quantity of medication in the dispensing machine 151. The computer processor 212 also updates or alters the information 109 in the information strip 100 for that cassette to indicate that the quantity of medication 5 in the cassette 10 has been reduced by the predetermined amount or quantity. The computer processor 212 also alters the information strip 100 to indicate the name of the physician that ordered that dose of medication and the name of the healthcare worker that dispensed the medication. Other information can also be written to the information strip 100, such as via the keyboard 216.

The predetermined dose of dispensed medication 5 falls into portable container 190. The computer processor 212 then updates or alters the information 199 in its associated information device 195 via reading and writing mechanism 200. The information 199 transmitted to this information device 195 comes from the information strip 100, keyboard 216, or hospital or pharmacy databases 222 and 224.

The portable container 190 and information device 195 are secured together to lock the medication 5 inside the portable container during transport to the patient 240. Once the portable container is brought to the patient 240, the patient information in the information device 195 is compared to the patient information 249 in the wrist band 242 of the patient to determine that the medication is being given to the appropriate patient for whom the medication was prescribed. Consumption information 119c is obtained by the information device 195, such as the time the medication 5 was administered, the name of the administering healthcare worker, and the actual quantity of the medication dose given to the patient for consumption. The portable container 190 and information device 195 are then returned to the pharmacy workstation 120 or the hospital floor workstation 150. The information 199 in the information device 195 is then downloaded into the administration and pharmacy databases 222 and 224 via workstations 120 or 150. Unused medication 5 is returned to the bulk containers 110.

Figure 30:
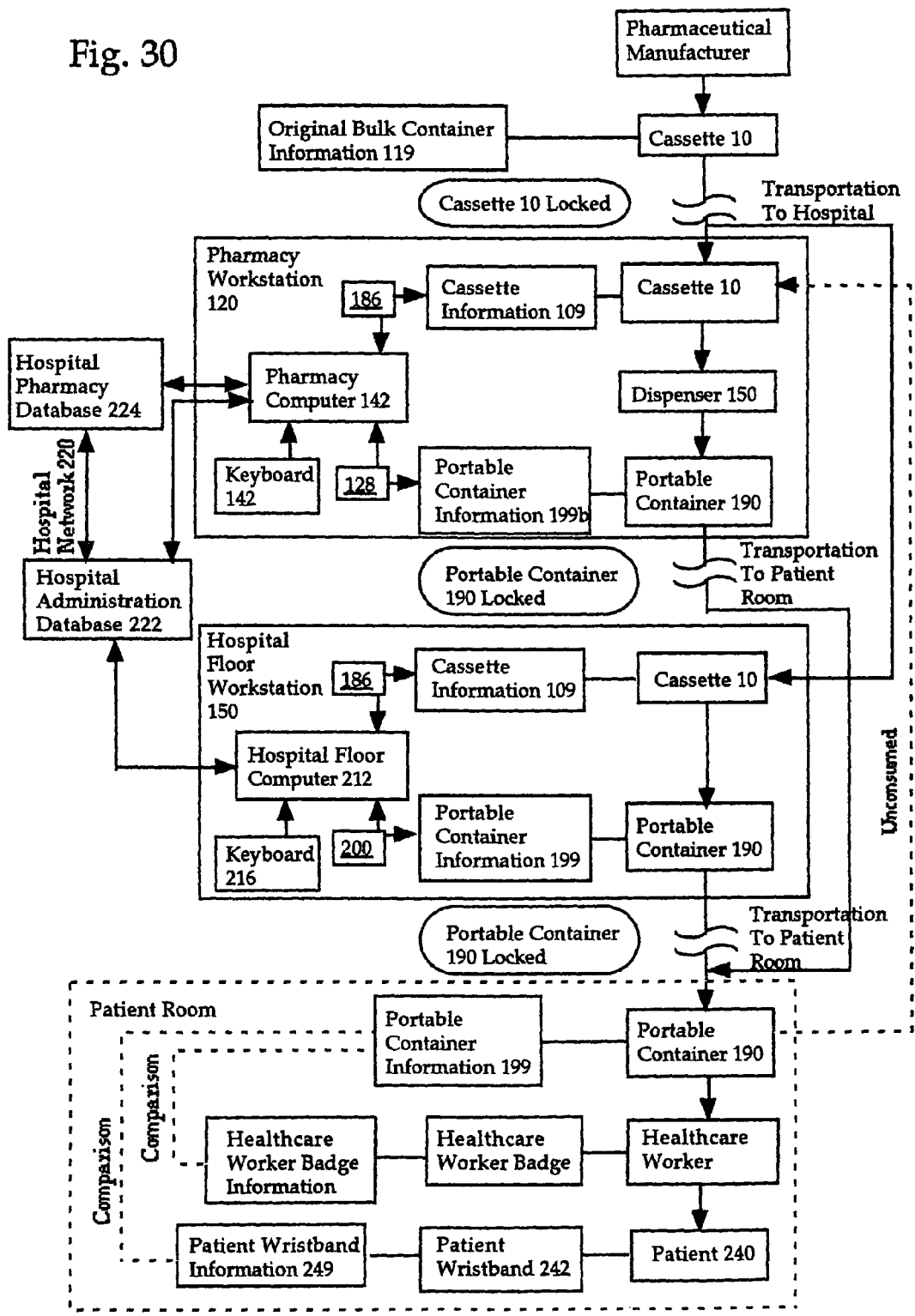
FIG. 30 is a flow chart showing a process of distributing medication and transferring information from a pharmaceutical manufacturer supplied cassette to either the hospital pharmacy or floor workstation, and from the hospital pharmacy or floor workstation to the portable container that is taken to the patient room for administering the medication to the patient.

Operation when Cassettes 10, 300 or 400 Supplied Directly By Pharmaceutical Manufacturer As shown in FIG. 30, the medication dispensing and information transfer process is somewhat simplified when the pharmaceutical manufacturer supplies medication to the hospital pharmacy 120 directly in cassettes 10, 300 or 400. The cassettes 10, 300 or 400 take the place of the bulk containers 110. The cassettes 10, 300 or 400 are either brought to the hospital pharmacy 120, as were the bulk containers 110, or are brought directly to the hospital floor workstation 150 and inserted into dispensing machine 151. The cassettes 10, 300 or 400 brought directly to the hospital floor workstation 150 are locked closed by the pharmaceutical manufacturer. The dispensing machine 121 or 151 dispenses the medication 5 from the cassette 10, 300 or 400 into the portable container 195.

When shipped to the hospital pharmacy, the information strips 100, 340 or 460 of cassettes 10, 300 or 400 only contain the information 119a supplied by the pharmaceutical manufacturer. Upon arrival at the hospital pharmacy, the information 119 in the cassette 10, 300 or 400, such as cassette medication quantity information, is conveyed to the hospital administration and hospital pharmacy data base 222 and 224 via the pharmacy or floor workstation 120 or 150. Additional information 109 is added to the information strip 100, 340 or 460 when dispensing the medication 5 to the portable container 190. This information 109 is sent to the information strip 100, 340 or 460 via the pharmacy or floor workstation 120 or 150. As previously discussed, the additional information 109 is entered via the pharmacy or floor computer processor 142 or 212, keyboard 142 or 216 or otherwise obtained from the hospital administration or pharmacy databases 222 or 224 via computer 142 or 212.

When the medication 5 is dispensed into the portable container 190 and information 199 is transmitted to the information device 195, the portable container is locked shut, transported to the room of the intended patient and administered to the patient in the process discussed above. Consumption information 199c is stored in the information device 195. The previously used cassette 10, 300 or 400 is returned to the hospital pharmacy for further use. Undispensed medication in the used cassettes 10, 300 or 400 returned from the dispensing machine 151 or unconsumed medication returned in the portable containers 190 can also be placed in other empty or partially filled cassettes 10, 300 or 400 already in the pharmacy. The information 119 in the information strip 100 of the refilled cassettes 10, 300 or 400 is updated via pharmacy workstation 120 to include desired new information 109 such as the quantity of medication placed in the refilled cassette.

Operation when Bulk Container 110 Dispensed Directly Into Portable Container 195

Figure 31:
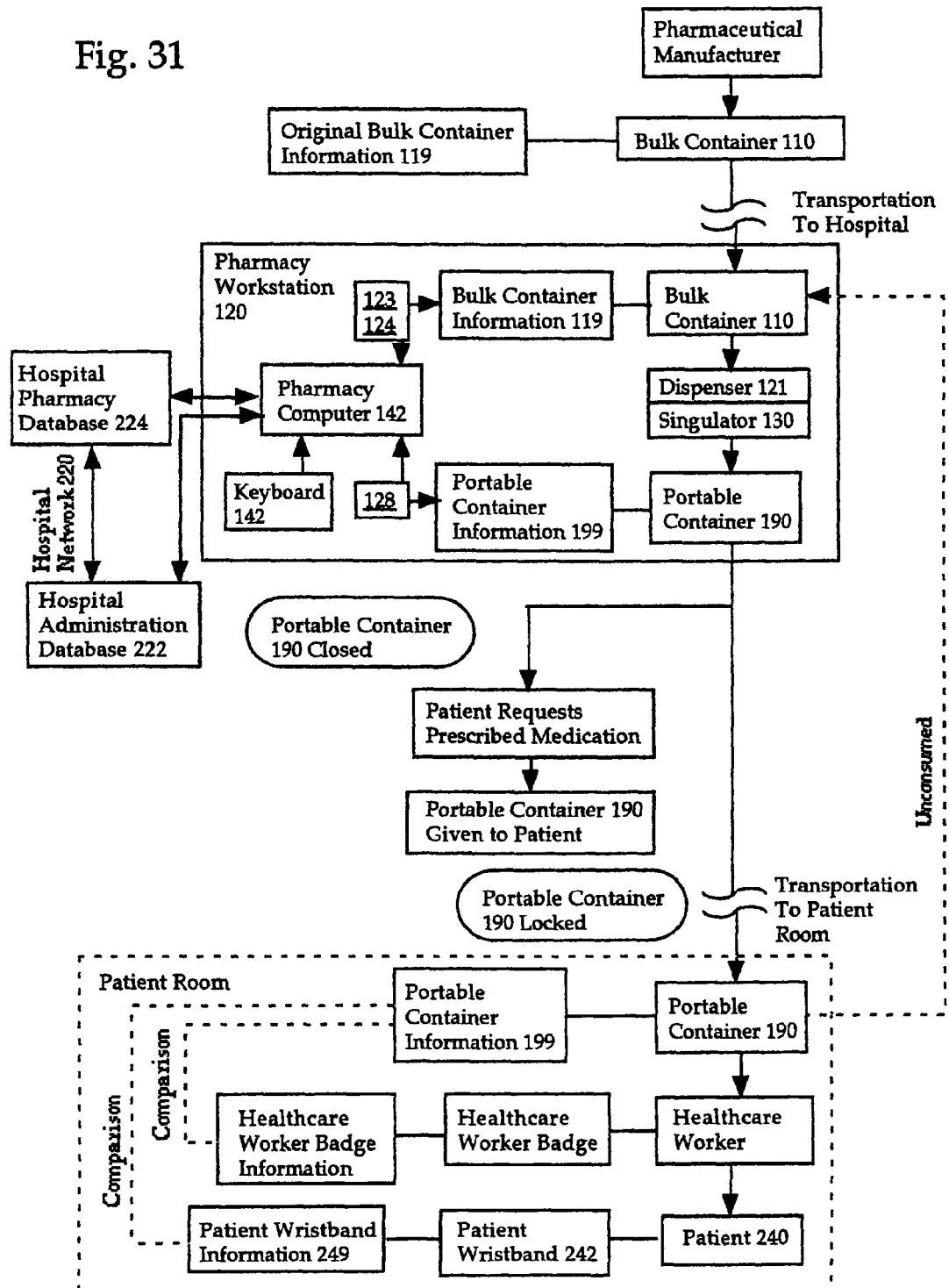
FIG. 31 is a flow chart showing a process of distributing medication and transferring information from a pharmaceutical manufacturer supplied bulk container to a hospital pharmacy, from the hospital pharmacy to the portable container that is either directly handed to the patient by the pharmacy staff or handed to a healthcare worker that takes it to the patient room for administering the medication to the patient.

As shown in FIG. 31, the dispensing and information transfer process is also somewhat simplified when the hospital pharmacy workstation 120 dispenses the medication 5 from the bulk container 110 directly into the portable container 195. This type of medication distribution and information transfer process is particularly useful in a smaller hospital or a retail pharmacy situation where there is little or no need for the hospital floor workstation 150. In the case of a retain pharmacy, the portable container 190 could be substituted with a pill vial type container (not shown) having its own associated information strip 100. Information 109 and 119 is transferred to the information device 195 or pill vial information strip 100 via the pharmacy workstation 120. In the small hospital situation, unconsumed medication is returned to the pharmacy workstation 120 in the same manner as discussed above. In the retail pharmacy situation where medication is dispensed into the pill vial and given to a patient for home use outside the control of the pharmacy, unconsumed medication is discarded for safety reasons.

It should also be understood that the invention as a whole may be embodied in other specific forms without departing from the spirit or central characteristics thereof. The present examples and embodiments thereof are to be considered in all aspects as illustrative and not restrictive, and the invention is not to be limited to the details given herein. It will be understood by those of skill in the art that various changes may be made and equivalents may be substituted without departing from the broader aspects of the invention. Specifically, while the invention has been shown and described as including a cassette, cartridge or multi-dose blister pack, it should be understood that other forms of containers could be used with equal effectiveness. It should therefore be understood that the container could take on a variety of shapes and forms without departing from the broad aspects of the invention.

I claim:

1. A medication distribution and information system for distributing a specific medication and coupling corresponding medication information to the specific medication during distribution, said medication distribution and information system comprising:
   a dispensing machine having an associated computer processor and a sensing mechanism for obtaining and transmitting information to and from said computer processor, said computer processor controlling said dispensing of medication by said dispensing machine;
   a first container holding the specific medication and having a machine readable electronic label containing the corresponding medication information;
   a second container having a machine readable and writable information strip;
   said first and second containers being joinable with said dispensing machine, and said sensing mechanism being alignable with said electronic label and said information strip;
   said specific medication being dispensable from said first container to said second container, said specific medication information being transferable from said electronic label to said information strip and said information strip being alterable to include said specific medication information;
   said second container being removable from said dispensing machine for distribution, said second container containing said specific medication and said information strip containing said specific medication information.

2. The medication distribution and information system of claim 1, and wherein said medication information includes medication type information to facilitate identifying said type of medication in said second container.

3. The medication distribution and information system of claim 1, and wherein said medication information includes pharmaceutical manufacturer name and batch identification information to facilitate a recall of said specific medication in said second container.

4. The medication distribution and information system of claim 1, and further comprising:
- a second dispensing machine having a second computer processor and a second sensing mechanism for obtaining and transmitting information to and from said second computer processor, said second computer processor controlling dispensing of medication by said second dispensing machine;
- a third container having a second machine readable and writable information strip, and said second dispensing machine being adapted to dispense said specific medication from said second container to said third container;
- said second and third containers being joinable with said second dispensing machine, and said information strip and said second information strip being alignable with said sensing mechanism;
- said specific medication being dispensable from said second container to said third container, and said specific medication information being transferable from said information strip of said second container to said information strip of said third container;
- said information strip of said third container being alterable to include said specific medication information; and,
- said third container being removable from said second dispensing machine for further distribution, said third container containing said specific medication and said information strip of said third container containing said specific medication information.

5. The medication distribution and information system of claim 4, and wherein said dispensing machine dispenses a specific quantity of said specific medication to said second container, said dispensing machine altering said information strip to include said medication quantity information, said second dispensing machine receiving said medication quantity information from said second container to facilitate maintaining an inventory of said specified medication in said second dispensing machine.

6. The medication distribution and information system of claim 5, and wherein said dispensing machine is a pharmacy dispensing machine and said second dispensing machine is a hospital floor dispensing machine.

7. A medication distribution and inventory system comprising:
- first and second containers, said first container holding a specific quantity of medication and having a machine readable electronic label containing medication information corresponding to the medication and including specific quantity information, said second container having a machine readable and writable information strip;
- first and second dispensing machines, said first dispensing machine being adapted to dispense the medication from said first container to said second container and transmit said medication information from said electronic label to said information strip, and said first and second dispensing machines being in communication with a common data base;
- said first and second containers being joinable with said first dispensing machine;
- a desired quantity of the medication being dispensable from said first container to said second container;
- said information strip being alterable to include said medication information including desired quantity information corresponding to said desired quantity of the medication;
- said desired quantity information being transmittable to said data base, and updating said data base to indicate a reduction of the medication in said first container and an increase of the medication in said second container by said desired quantity of the medication;
- said second container being removable from said first dispensing machine and transportable to said second dispensing machine;
- said second container being joinable with said second dispensing machine; and,
- said data base being updatable to indicate an increase of the medication in said second dispensing machine by said desired quantity of medication; and,
- said data base being adapted to maintain an inventory of said medication in said first and second containers and second dispensing machine.

* * * * *